(12) United States Patent
McGall et al.

(10) Patent No.: US 6,596,856 B2
(45) Date of Patent: Jul. 22, 2003

(54) NUCLEIC ACID LABELING COMPOUNDS

(75) Inventors: Glenn McGall, Mountain View, CA (US); Anthony D. Barone, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 70 days.

(21) Appl. No.: 09/780,574

(22) Filed: Feb. 9, 2001

(65) Prior Publication Data

US 2001/0044531 A1 Nov. 22, 2001

Related U.S. Application Data

(63) Continuation-in-part of application No. 09/126,645, filed on Jul. 31, 1998, now abandoned.

(51) Int. Cl.$^7$ ...................... C07H 27/00; C07H 19/052; C07H 21/02; C07H 21/04

(52) U.S. Cl. .................. 536/25.32; 536/22.1; 536/24.2; 536/25.3; 435/6

(58) Field of Search .............................. 435/6; 536/24.2, 536/22.1, 25.3, 25.32

(56) References Cited

U.S. PATENT DOCUMENTS

| | | | |
|---|---|---|---|
| 4,981,783 A | 1/1991 | Augenlicht | 435/6 |
| 5,002,867 A | 3/1991 | Macevicz | 435/6 |
| 5,143,854 A | 9/1992 | Pirrung et al. | 436/518 |
| 5,173,260 A | 12/1992 | Zander et al. | 422/57 |
| 5,202,231 A | 4/1993 | Drmanac et al. | 435/6 |
| 5,324,633 A | 6/1994 | Fodor et al. | 435/6 |
| 5,422,241 A | 6/1995 | Goldrick et al. | 435/6 |
| 5,543,292 A | 8/1996 | Imai et al. | 435/6 |
| 5,571,639 A | 11/1996 | Hubbell et al. | 430/5 |
| 6,174,998 B1 | 1/2001 | Muhlegger et al. | 536/4.1 |
| 6,211,158 B1 | 4/2001 | Seela et al. | 514/44 |

FOREIGN PATENT DOCUMENTS

| | | | |
|---|---|---|---|
| EP | 0132621 | 2/1985 | ............ C12Q/1/68 |
| EP | 059719 | 10/1985 | ............ C12Q/1/68 |
| EP | 0266787 | 5/1988 | ............ C12Q/1/68 |
| EP | 0320308 | 6/1989 | ............ C12Q/1/68 |
| EP | 0322311 | 6/1989 | ............ C12Q/1/68 |
| EP | 0336731 | 10/1989 | ............ C12Q/1/68 |
| EP | 0535242 | 4/1993 | ............ C12Q/1/68 |
| EP | 0717113 | 6/1996 | ............ C12Q/1/68 |
| EP | 0721016 | 7/1996 | ............ C12Q/1/68 |
| WO | 89/10977 | 11/1989 | ............ C12Q/1/68 |
| WO | 90/00626 | 1/1990 | ............ C12Q/1/68 |
| WO | 90/04652 | 5/1990 | ............ C12Q/1/68 |
| WO | 95/00530 | 5/1992 | ............ C07H/21/04 |
| WO | 92/10092 | 6/1992 | ............ A01N/1/02 |
| WO | 93/17126 | 9/1993 | ............ C12Q/1/68 |
| WO | 95/04594 | 2/1995 | ............ B01L/3/00 |
| WO | 95/04833 | 2/1995 | ............ C12Q/1/68 |
| WO | 95/04834 | 2/1995 | ........... C12Q/1/682 |
| WO | 95/20681 | 8/1995 | ............ C12Q/1/68 |
| WO | 95/30774 | 11/1995 | ............ C12Q/1/68 |
| WO | 95/35505 | 12/1995 | ......... G01N/33/543 |
| WO | 98/11104 | 3/1998 | ......... C07D/405/04 |

OTHER PUBLICATIONS

Broude, N. E., et al., "Enhanced DNA sequencing by hybridization", *PNAS, 91*, pp. 3072–3076, (Apr. 1994).

(List continued on next page.)

*Primary Examiner*—James O. Wilson
*Assistant Examiner*—Josephine Young
(74) *Attorney, Agent, or Firm*—Schwegman, Lundberg, Woessner & Kluth, P.A.; Thomas E. Malone; Phil L. McGarrigle

(57) ABSTRACT

Nucleic acid labeling compounds containing heterocyclic derivatives are disclosed. The heterocyclic derivative containing compounds are synthesized by condensing a heterocyclic derivative with a cyclic group (e.g. a ribofuranose derivative). The labeling compounds are suitable for enzymatic attachment to a nucleic acid, either terminally or internally, to provide a mechanism of nucleic acid detection.

27 Claims, 14 Drawing Sheets

OTHER PUBLICATIONS

Eggers, M., et al., "A Microchip for Quantitative Detection of Molecules Utilizing Luminescent and Radioisotope Reporter Groups", *BioTechniques, 17* (*3*), pp. 516–525, (Sep. 1994.)

Feldman, W., et al., "Gray Code Masks for Sequencing by Hybridization", *Genomics, 23*, pp. 233–235, (1994).

Fodor, et al., "Light–directed, spatially addressable parallel chemical synthesis", *Science, 251*, pp. 767–773, (1991).

Hoheisel, J.D., "Application of Hybridization Techniques to Genome Mapping and Sequencing", *Trends in Genetics, 10* (*3*), pp. 79–83, (Mar. 1994).

Kallioniemi, A., et al., "Comparative Genomic Hybridization for Molecular Cytogenetic Analysis of Solid Tumors", *Science, 258*, pp. 818–821, (Oct. 1992).

Khrapko, K.R., et al., "An Oligonucleotide Hybridization Approach to DNA Sequencing", *FEBS Letters, 256*, pp. 118–122, (Oct. 1989).

Lennon, G.G., et al., "Hybridization analyses of arrayed cDNA libraries", *Trends in Genetics, 7* (*10*), pp. 314–317, (Oct. 1991).

Lipshutz, R.J., et al., "Using Oligonucleotide Probe Arrays to Access Genetic Diversity", *Biotechniques, 19* (*3*), pp. 442–447, (1995).

Lockhart, D.J., et al., "Expression monitoring by hybridization to high–density oligonucleotide arrays", *Nature Biotechnology, 14* (*13*), pp. 1675–1680, (Dec. 1996).

Pevzner, P.A., et al., "Improved Chips for Sequencing by Hybridization", *Journal of Biomolecular Structure & Dynamics, 9* (*2*), pp. 399–410, (1991).

Schena, M., et al., "Parallel human gemone analysis: Microarray–based expression monitoring of 1000 genes", *PNAS, 93*, pp. 10614–10619, (Oct. 1996).

Southern, et al., "Analyzing and comparing nucleic acid sequences by hybridization to arrays of oligonuceotides: evaluation using experimental models", *Genomics, 13*, pp. 1008–1017, (1992).

Southern, E.M., et al., "Arrays of complementary oligonucleotides for analysing the hybridisation behaviour of nucleic acids", *Nucleic Acids Research, 22* (*8*), pp. 1368–1373, (1994).

Stimpson, D. I., et al., "Real–Time Detection of DNA Hybridization and Melting on Oligonucleotide Arrays by Using Optical Wave Guides", *PNAS, 92*, pp. 6379–6383, (Jul. 1995).

Pankiewicz, K.W., "Selective Methylation of the C–Nucleoside, ψ–Isocytidine and its 2'–Deoxy Analog. Synthesis of 1–Methyl, 3–Methyl and 4–O–Methyl Derivatives", *Tetrahedron* vol. 40, No. 1, (1984), pp. 33–38.

NUCLEIC ACID LABELING COMPOUNDS

RELATED APPLICATIONS

This application is a continuation-in-part of U.S. Ser. No. 09/126,645, filed Jul. 31, 1998 now abandoned (which is herein incorporated by reference).

STATEMENT OF RIGHTS TO INVENTIONS MADE UNDER FEDERALLY SPONSORED RESEARCH

This invention was made with Government support under contract 70NANB5H1031 awarded by the Advanced Technology Program of the National Institute of Standards and Technology. The Government has certain rights in this invention.

BACKGROUND OF THE INVENTION

Gene expression in diseased and healthy individuals is oftentimes different and characterizable. The ability to monitor gene expression in such cases provides medical professionals with a powerful diagnostic tool. This form of diagnosis is especially important in the area of oncology, where it is thought that the overexpression of an oncogene, or the underexpression of a tumor suppressor gene, results in tumorogenesis. See Mikkelson et al. *J. Cell. Biochem.* 1991, 46, 3–8.

One can indirectly monitor gene expression, for example, by measuring a nucleic acid (e.g., mRNA) that is the transcription product of a targeted gene. The nucleic acid is chemically or biochemically labeled with a detectable moiety and allowed to hybridize with a localized nucleic acid probe of known sequence. The detection of a labeled nucleic acid at the probe position indicates that the targeted gene has been expressed. See International Application Publication Nos. WO 97/27317, WO 92/10588 and WO 97/10365.

The labeling of a nucleic acid is typically performed by covalently attaching a detectable group (label) to either an internal or terminal position. Scientists have reported a number of detectable nucleotide analogues that have been enzymatically incorporated into an oligo- or polynucleotide. Langer et al., for example, disclosed analogues of dUTP and UTP that contain a covalently bound biotin moiety. *Proc. Natl. Acad. Sci. USA* 1981, 78, 6633–6637. The analogues, shown below, possess an allylamine linker arm that is attached to the C-5 position of the pyrimidine ring. The dUTP and UTP analogues, wherein R is H or OH, were incorporated into a polynucleotide.

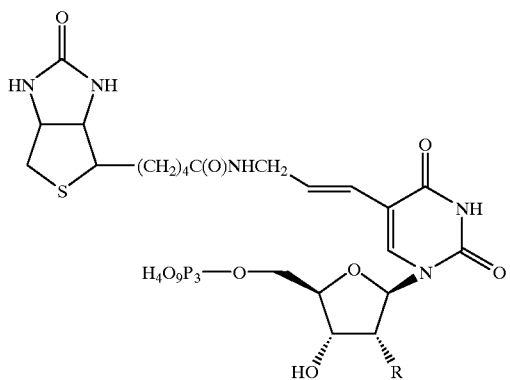

Petrie et al. disclosed a dATP analogue, 3-[5-[(N-biotinyl-6-aminocaproyl)-amino]pentyl]-1-(2-deoxy-β-D-erythro-pentofuranosyl)-1H-pyrazolo[3,4-d]pyrimidin-4-amine-5'-triphosphate. *Bioconjugate Chem.* 1991, 2, 441–446. The analogue, shown below, is modified at the 3-position with a linker arm that is attached to a biotin moiety. Petrie et al. reported that the compound wherein R is biotin is incorporated into DNA by nick translation.

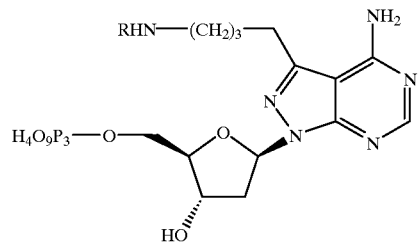

Prober et al. disclosed a set of four dideoxynucleotides, each containing a succinylfluorescein dye. *Science* 1987, 238, 336–341. The dideoxynucleotides, one of which is shown below, were enzymatically incorporated into an oligonucleotide through a template directed extension of a primer. The compounds provided for a DNA sequencing method based on gel migration.

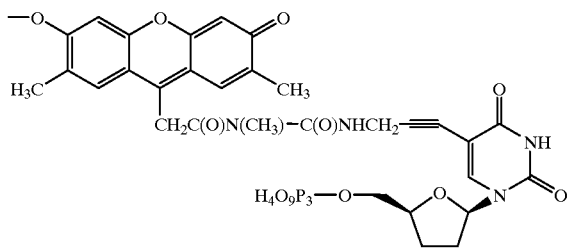

Herrlein et al. disclosed modified nucleoside trisphosphates of the four DNA bases. *Helv. Chim. Acta* 1994, 77, 586–596. The compounds, one of which is shown below, contain a 3'-amino group containing radioactive or fluorescent moieties. Herrlein et al. further described the use of the nucleoside analogues as DNA chain terminators.

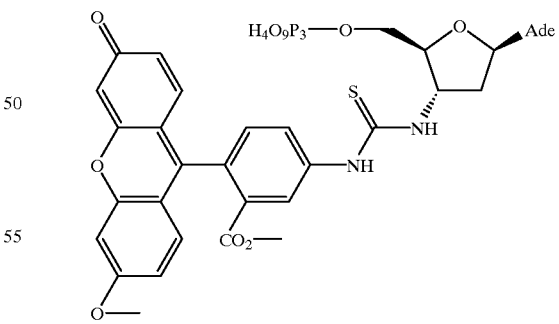

Cech et al. disclosed 3'-amino-functionalized nucleoside triphosphates. *Collect. Czech. Chem. Commun.* 1996, 61, S297–S300. The compounds, one of which is shown below, contain a fluorescein attached to the 3'-position through an amino linker. Cech et al. proposed that the described functionalized nucleosides would be useful as terminators for DNA sequencing.

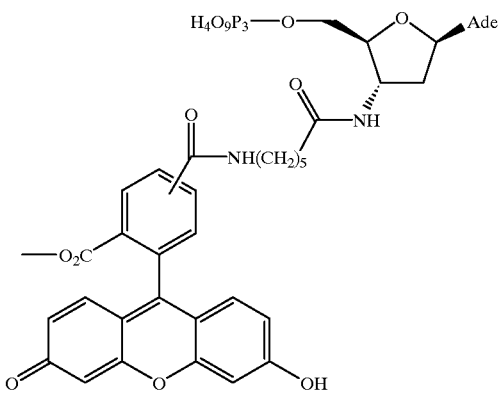

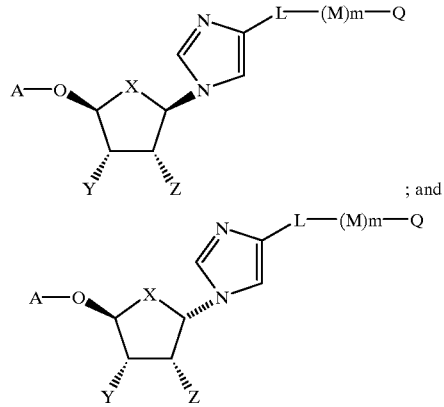
; and

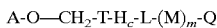

DISCLOSURE OF THE INVENTION

The present invention relates to nucleic acid labeling compounds. More specifically, the invention provides heterocyclic derivatives containing a detectable moiety. The invention also provides methods of making such heterocyclic derivatives. It further provides methods of attaching the heterocyclic derivatives to a nucleic acid.

The development of a novel nucleic acid labeling compound that is effectively incorporated into a nucleic acid to provide a readily detectable composition would benefit genetic analysis technologies. It would aid, for example, in the monitoring of gene expression and the detection and screening of mutations and polymorphisms. Such a compound should be suitable for enzymatic incorporation into a nucleic acid. Furthermore, the nucleic acid to which the labeling compound is attached should maintain its ability to bind to a probe, such as a complementary nucleic acid.

The present invention provides nucleic acid labeling compounds that are capable of being enzymatically incorporated into a nucleic acid. The nucleic acids to which the compounds are attached maintain their ability to bind to a complementary nucleic acid sequence.

The nucleic acid labeling compounds of the present invention are of the following structure:

A-O—CH$_2$-T-H$_c$-L-(M)$_m$-Q wherein A is hydrogen or a functional group that permits the attachment of the nucleic acid labeling compound to a nucleic acid; T is a template moiety; H$_c$ is a heterocyclic group; L is a linker moiety; Q is a detectable moiety; and M is a connecting group, wherein m is an integer ranging from 0 to about 5.

In one embodiment, the nucleic acid labeling compounds have the following structures:

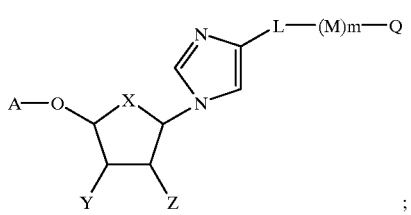
;

wherein A is H or a functional group that permits the attachment of the nucleic acid labeling compound to a nucleic acid;

X is O, S, NR$_1$ or CHR$_2$, wherein R$_1$ and R$_2$ are, independently, H, alkyl or aryl; Y is H, N$_3$, F, OR$_9$, SR$_9$ or NHR$_9$, wherein R$_9$ is H, alkyl or aryl; Z is H, N$_3$, F or OR$_{10}$, wherein R$_{10}$ is H, alkyl or aryl; L is is amido alkyl; Q is a detectable moiety; and, M is a connecting group, wherein m is an integer ranging from 0 to about 3.

In another embodiment, A is H or H$_4$O$_9$P$_3$—; X is O; Y is H or OR$_9$, wherein R$_9$ is H, alkyl or aryl; Z is H, N$_3$, F or OR$_{10}$, wherein R$_{10}$ is H, alkyl or aryl; L is —C(O)NH(CH$_2$)$_n$NH—, wherein n is an integer ranging from about 2 to about 10; Q is biotin or a carboxyfluorescein; and, M is —CO(CH$_2$)$_5$NH—, wherein m is 1 or 0.

In another embodiment, Y is H or OH; Z is H or OH; L is —C(O)NH(CH$_2$)$_4$NH—; Q is biotin; and, M is —CO(CH$_2$)$_5$NH, wherein m is 1.

In another embodiment, Y is H or OH; Z is H or OH; L is —C(O)NH(CH$_2$)$_4$NH—; Q is 5-carboxyfluorescein; and, m is 0.

In one embodiment, the nucleic acid labeling compounds have the following structures:

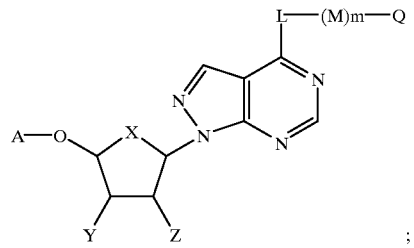
;

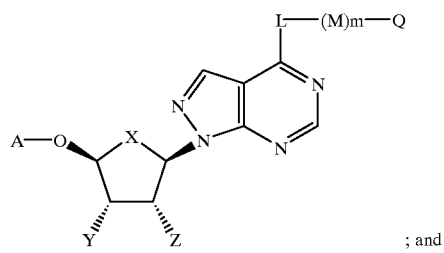
; and

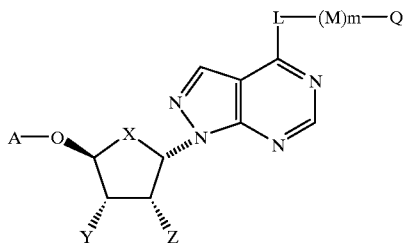

wherein A is H or a functional group that permits the attachment of the nucleic acid labeling compound to a nucleic acid; X is O, S, $NR_1$ or $CHR_2$, wherein $R_1$ and $R_2$ are, independently, H, alkyl or aryl; Y is H, $N_3$, F, $OR_9$, $SR_9$ or $NHR_9$, wherein $R_9$ is H, alkyl or aryl; Z is H, $N_3$, F or $OR_{10}$, wherein $R_{10}$ is H, alkyl or aryl; L is amino alkyl; Q is a detectable moiety; and, M is a connecting group, wherein m is an integer ranging from 0 to about 3.

In another embodiment, A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —$NH(CH_2)_n$NH—, wherein n is an integer ranging from about 2 to about 10; Q is biotin or carboxyfluorescein; and, M is —$CO(CH_2)_5$NH— or —$CO(CH_2)_5NHCO(CH_2)_5NH$—, wherein m is 1 or 0.

In another embodiment, Y is H or OH; Z is H or OH; L is —$NH(CH_2)_4NH$—; Q is biotin; and, m is 0.

In another embodiment, Y is H or OH; Z is H or OH; L is —$NH(CH_2)_4NH$—; Q is 5-carboxyfluorescein; and, m is 0.

In one embodiment, the nucleic acid labeling compounds have the following structures:

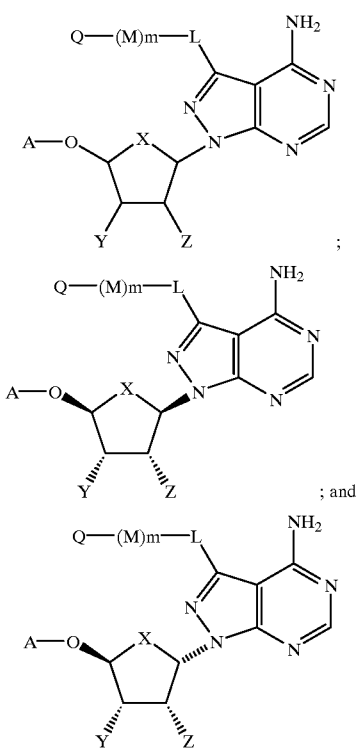

wherein A is H or a functional group that permits the attachment of the nucleic acid labeling compound to a nucleic acid; X is O, S, $NR_1$ or $CHR_2$, wherein $R_1$ and $R_2$ are, independently, H, alkyl or aryl; Y is H, $N_3$, F, $OR_9$, $SR_9$ or $NHR_9$, wherein $R_9$ is H, alkyl or aryl; Z is H, $N_3$, F or $OR_{10}$, wherein $R_{10}$ is H, alkyl or aryl; L is alkynyl alkyl; Q is a detectable moiety; and, M is a connecting group, wherein m is an integer ranging from 0 to about 3.

In another embodiment, A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —C≡$C(CH_2)_n$NH—, wherein n is an integer ranging from about 1 to about 10; Q is biotin or carboxyfluorescein; and, M is —$CO(CH_2)_5$NH—, wherein m is 1 or 0.

In another embodiment, Y is H or OH; Z is H or OH; L is —C≡$CCH_2NH$—; Q is biotin; and, m is 1.

In another embodiment, Y is H or OH; Z is H or OH; L is —C≡$CCH_2NH$—; Q is 5-carboxyfluorescein; and, m is 1.

In one embodiment, the nucleic acid labeling compounds have the following structures:

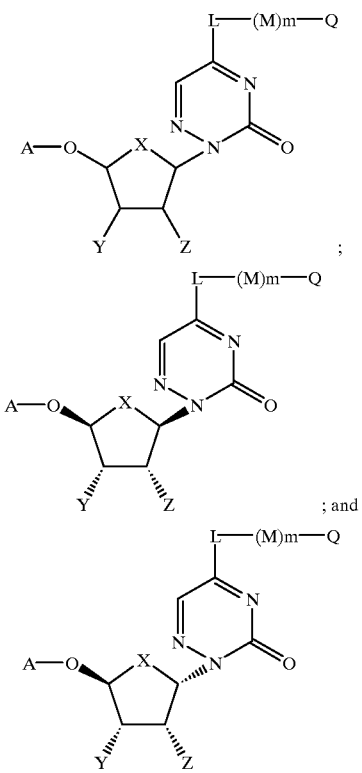

wherein A is H or a functional group that permits the attachment of the nucleic acid labeling compound to a nucleic acid; X is O, S, $NR_1$ or $CHR_2$, wherein $R_1$ and $R_2$ are, independently, H, alkyl or aryl; Y is H, $N_3$, F, $OR_9$, $SR_9$ or $NHR_9$, wherein $R_9$ is H, alkyl or aryl; Z is H, $N_3$, F or $OR_{10}$, wherein $R_{10}$ is H, alkyl or aryl; L is amino alkyl; Q is a detectable moiety; and, M is a connecting group, wherein m is an integer ranging from 0 to about 3.

In another embodiment, A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —$NH(CH_2)_n$NH—, wherein n is an integer ranging from about 2 to about 10; Q is biotin or carboxyfluorescein; and, M is —$CO(CH_2)_5$NH— or —$CO(CH_2)_5NHCO(CH_2)_5NH$—, wherein m is 1 or 0.

In another embodiment, Y is H or OH; Z is H or OH; L is —$NH(CH_2)_4NH$—; Q is biotin; and, M is —$CO(CH_2)_5NH$—, wherein m is 1.

In another embodiment, Y is H or OH; Z is H or OH; L is —NH(CH$_2$)$_4$NH—; Q is 5-carboxyfluorescein; and, M is —CO(CH$_2$)$_5$NH—, wherein m is 1.

In one embodiment, the nucleic acid labeling compounds have the following structures:

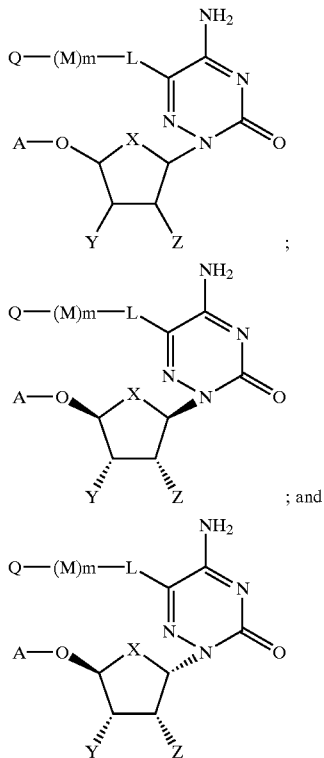

wherein A is H or a functional group that permits the attachment of the nucleic acid labeling compound to a nucleic acid; X is O, S, NR$_1$ or CHR$_2$, wherein R$_1$ and R$_2$ are, independently, H, alkyl or aryl; Y is H, N$_3$, F, OR$_9$, SR$_9$ or NHR$_9$, wherein R$_9$ is H, alkyl or aryl; Z is H, N$_3$, F or OR$_{10}$, wherein R$_{10}$ is H, alkyl or aryl; L is functionalized alkyl, alkenyl alkyl or alkynyl alkyl; Q is a detectable moiety; and, M is a connecting group, wherein m is an integer ranging from 0 to about 3.

In another embodiment, A is H or H$_4$O$_9$P$_3$—; X is O; Y is H or OR$_9$, wherein R$_9$ is H, alkyl or aryl; Z is H, N$_3$, F or OR$_{10}$, wherein R$_{10}$ is H, alkyl or aryl; L is —CH═CH(CH$_2$)$_n$NH—, wherein n is an integer ranging from about 1 to about 10; Q is biotin or carboxyfluorescein; and, M is —CO(CH$_2$)$_5$NH— or —CO(CH$_2$)$_5$NHCO(CH$_2$)$_5$NH—, wherein m is 1 or 0.

In another embodiment, Y is H or OH; Z is H or OH; L is —CH═CHCH$_2$NH—; Q is biotin; and, m is 0.

In another embodiment, Y is H or OH; Z is H or OH; L is —CH═CHCH$_2$NH—; Q is 5-carboxyfluorescein; and, m is 0.

In one embodiment, the nucleic acid labeling compounds have the following structures:

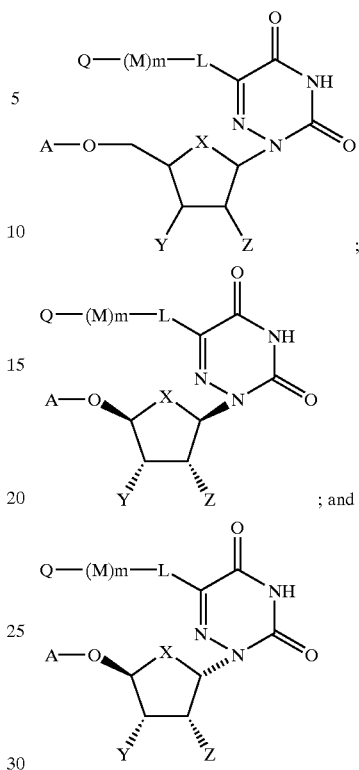

wherein A is H or a functional group that permits the attachment of the nucleic acid labeling compound to a nucleic acid; X is O, S, NR$_1$ or CHR$_2$, wherein R$_1$ and R$_2$ are, independently, H, alkyl or aryl; Y is H, N$_3$, F, OR$_9$, SR$_9$ or NHR$_9$, wherein R$_9$ is H, alkyl or aryl; Z is H, N$_3$, F or OR$_{10}$, wherein R$_{10}$ is H, alkyl or aryl; L is functionalized alkyl, alkenyl alkyl or alkynyl alkyl; Q is a detectable moiety; and, M is a connecting group, wherein m is an integer ranging from 0 to about 3.

In another embodiment, A is H or H$_4$O$_9$P$_3$—; X is O; Y is H or OR$_9$, wherein R$_9$ is H, alkyl or aryl; Z is H, N$_3$, F or OR$_{10}$, wherein R$_{10}$ is H, alkyl or aryl; L is —CH═CH(CH$_2$)$_n$NH—, wherein n is an integer ranging from about 1 to about 10; Q is biotin or carboxyfluorescein; and, M is —CO(CH$_2$)$_5$NH— or —CO(CH$_2$)$_5$NHCO(CH$_2$)$_5$NH—, wherein m is 1 or 0.

In another embodiment, Y is H or OH; Z is H or OH; L is —CH═CHCH$_2$NH—; Q is biotin; and, m is 0.

In another embodiment, Y is H or OH; Z is H or OH; L is —CH═CHCH$_2$NH—; Q is 5-carboxyfluorescein; and, m is 0.

The present invention also provides nucleic acid derivatives produced by coupling a nucleic acid labeling compound with a nucleic acid and hybridization products comprising the nucleic acid derivatives bound to a complementary probe.

In one embodiment, the nucleic acid labeling compounds used in the coupling have the following structures:

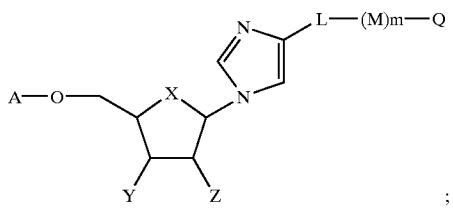

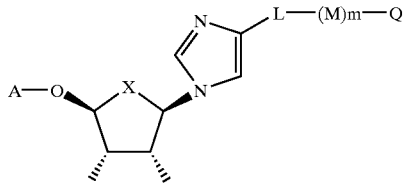
; and

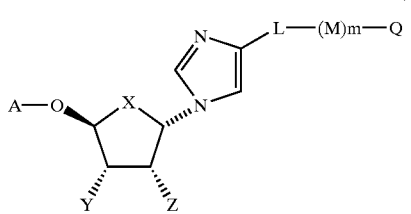

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkly or aryl; L is —C(O)NH(CH$_2$)$_n$NH—, wherein n is an integer ranging from about 2 to about 10; Q is biotin or a carboxyfluorescein; and, M is —CO(CH$_2$)$_5$NH—, wherein mn is 1 or 0.

The hybridization product formed from this nucleic acid derivative comprises the nucleic acid derivative bound to a complementary probe. In one embodiment, the probe is attached to a glass chip.

In another embodiment, the nucleic acid labeling compounds used in the coupling have the following structures:

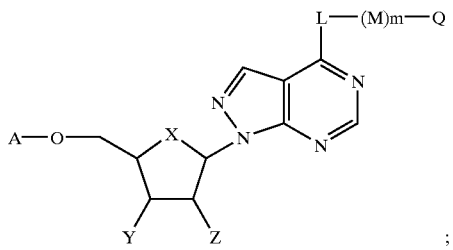

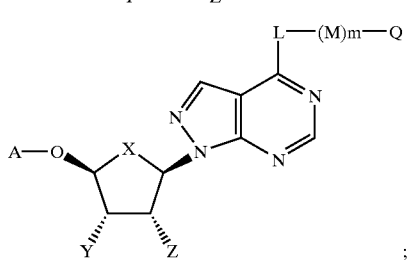
; and

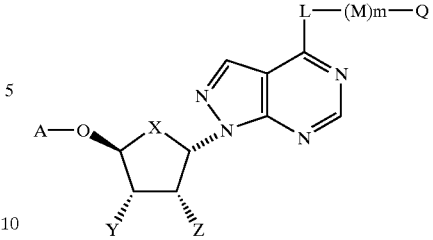

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —NH(CH$_2$)$_n$NH—, wherein n is an integer ranging from about 2 to about 10; Q is biotin or carboxyfluorescein; and, M is —CO(CH$_2$)$_5$NH— or —CO(CH$_2$)$_5$NHCO(CH$_2$)$_5$NH—, wherein m is 1 or 0.

The hybridization product formed from this nucleic acid derivative comprises the nucleic acid derivative bound to a complementary probe. In one embodiment, the probe is attached to a glass chip.

In another embodiment, the nucleic acid labeling compounds used in the coupling have the following structures:

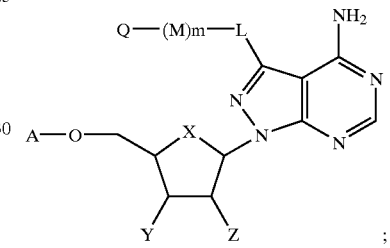
;

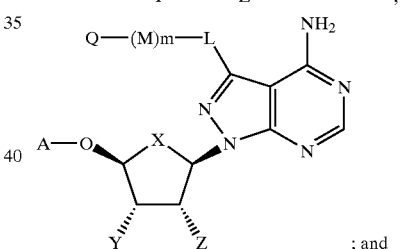
; and

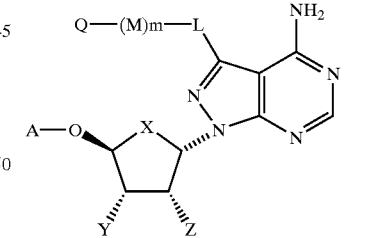

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —C≡C(CH$_2$)$_n$NH—, wherein n is an integer ranging from about 1 to about 10; Q is biotin or carboxyfluorescein; and, M is —CO(CH$_2$)$_5$NH—, wherein m is 1 or 0.

The hybridization product formed from this nucleic acid derivative comprises the nucleic acid derivative bound to a complementary probe. In one embodiment, the probe is attached to a glass chip.

In another embodiment, the nucleic acid labeling compounds used in the coupling have the following structures:

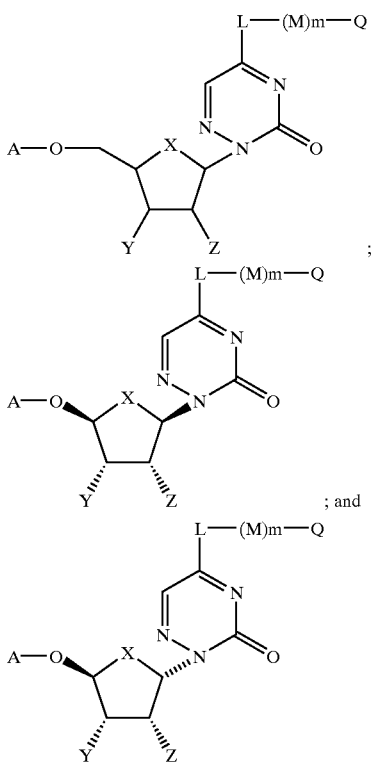

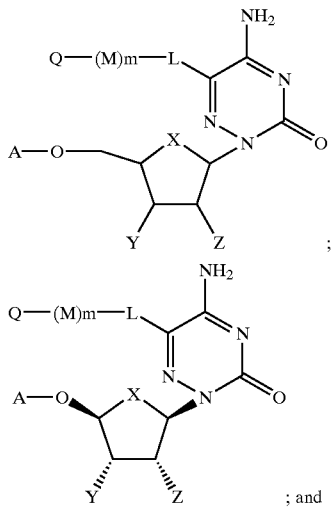

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —NH(CH$_2$)$_n$NH—, wherein n is an integer ranging from about 2 to about 10; Q is biotin or carboxyfluorescein; and, M is —CO(CH$_2$)$_5$NH— or —CO(CH$_2$)$_5$NHCO(CH$_2$)$_5$NH—, wherein m is 1 or 0.

The hybridization product formed from this nucleic acid derivative comprises the nucleic acid derivative bound to a complementary probe. In one embodiment, the probe is attached to a glass chip.

In another embodiment, the nucleic acid labeling compounds used in the coupling have the following structures:

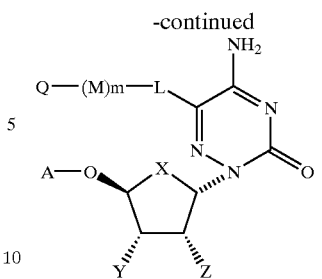

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —CH=CH(CH$_2$)$_n$NH—, wherein n is an integer ranging from about 1 to about 10; Q is biotin or carboxyfluorescein; and, M is —CO(CH$_2$)$_5$NH— or —CO(CH$_2$)$_5$NHCO(CH$_2$)$_5$NH—, wherein m is 1 or 0.

The hybridization product formed from this nucleic acid derivative comprises the nucleic acid derivative bound to a complementary probe. In one embodiment, the probe is attached to a glass chip.

In another embodiment, the nucleic acid labeling compounds used in the coupling have the following structures:

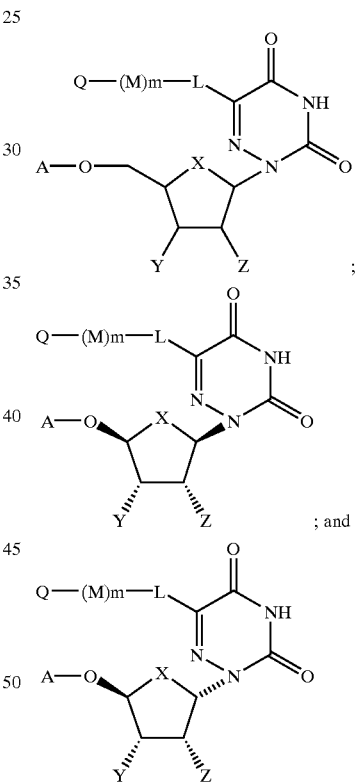

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —CH=CH(CH$_2$)$_n$NH—, wherein n is an integer ranging from about 1 to about 10; Q is biotin or carboxyfluorescein; and, M is —CO(CH$_2$)$_5$NH— or —CO(CH$_2$)$_5$NHCO(CH$_2$)$_5$NH—, wherein m is 1 or 0.

The hybridization product formed from this nucleic acid derivative comprises the nucleic acid derivative bound to a complementary probe. In one embodiment, the probe is attached to a glass chip.

The present invention also provides methods of synthesizing nucleic acid derivatives by attaching a nucleic acid labeling compound to a nucleic acid. It further provides methods of detecting nucleic acids involving incubating the nucleic acid derivatives with a probe.

In one embodiment, the nucleic acid labeling compounds attached to the nucleic acid have the following structures:

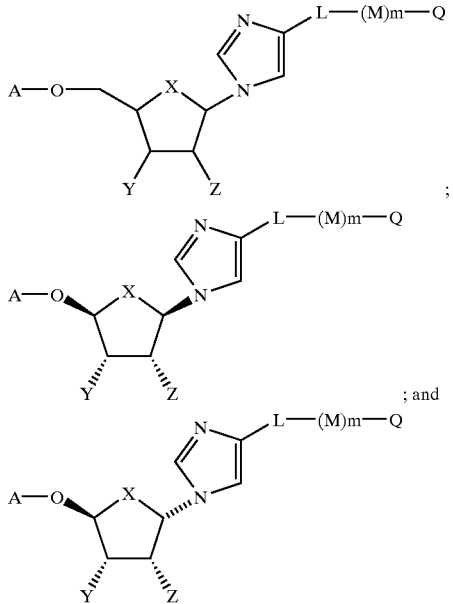

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —C(O)NH(CH$_2$)$_n$NH—, wherein n is an integer ranging from about 2 to about 10; Q is biotin or a carboxyfluorescein; and, M is —CO(CH$_2$)$_5$NH—, wherein m is 1 or 0.

The method of nucleic acid detection using the nucleic acid derivative involves the incubation of the derivative with a probe. In one embodiment, the probe is attached to a glass chip.

In one embodiment, the nucleic acid labeling compounds attached to the nucleic acid have the following structures:

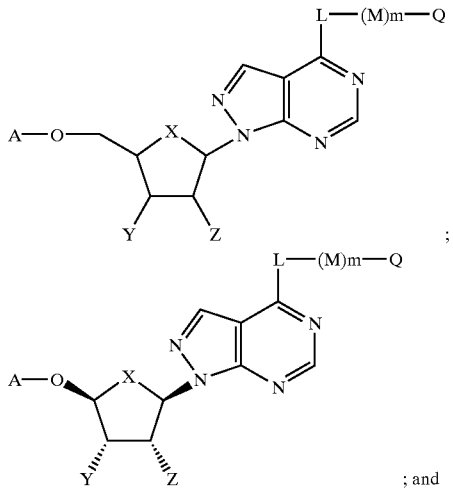

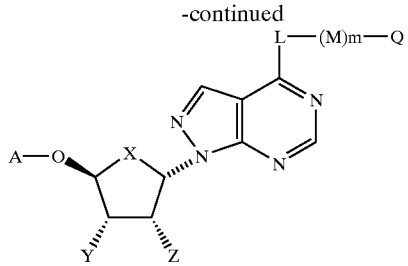

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —NH(CH$_2$)$_n$NH—, wherein n is an integer ranging from about 2 to about 10; Q is biotin or carboxyfluorescein; and, M is —CO(CH$_2$)$_5$NH— or —CO(CH$_2$)$_5$NHCO(CH$_2$)$_5$NH—, wherein m is 1 or 0.

The method of nucleic acid detection using the nucleic acid derivative involves the incubation of the derivative with a probe. In one embodiment, the probe is attached to a glass chip.

In one embodiment, the nucleic acid labeling compounds attached to the nucleic acid have the following structures:

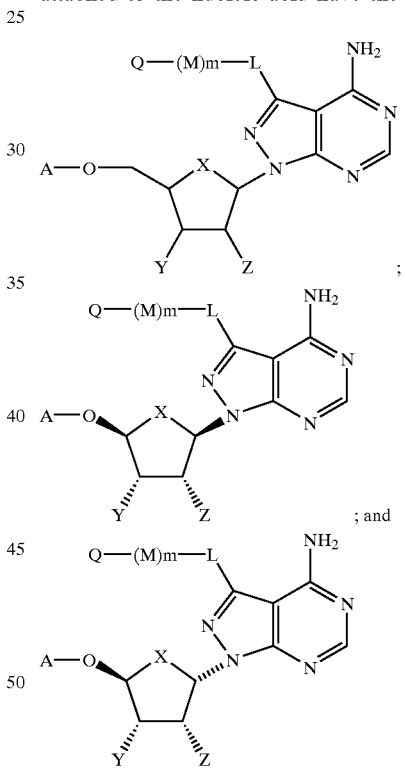

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —C≡C(CH$_2$)$_n$NH—, wherein n is an integer ranging from about 1 to about 10; Q is biotin or carboxyfluorescein; and, M is —CO(CH$_2$)$_5$NH—, wherein m is 1 or 0.

The method of nucleic acid detection using the nucleic acid derivative involves the incubation of the derivative with a probe. In one embodiment, the probe is attached to a glass chip.

In one embodiment, the nucleic acid labeling compounds attached to the nucleic acid have the following structures:

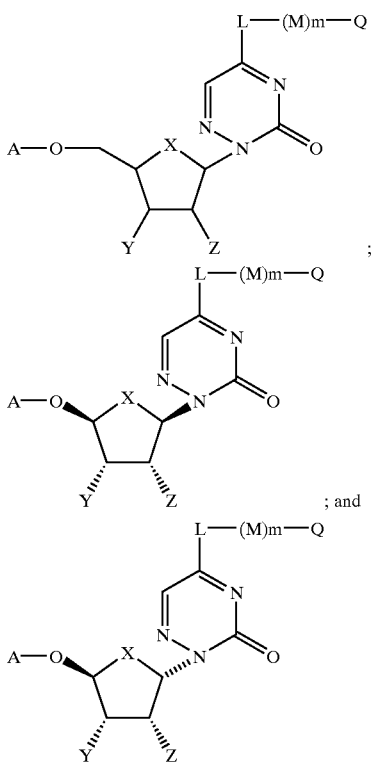

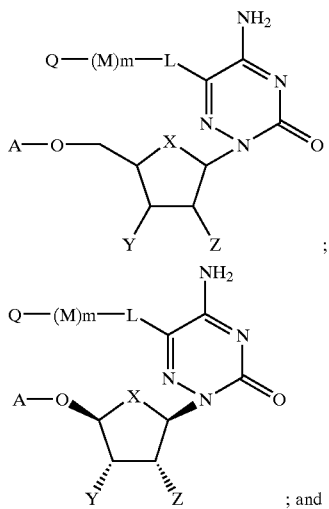

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —NH(CH$_2$)$_n$NH—, wherein n is an integer ranging from about 2 to about 10; Q is biotin or carboxyfluorescein; and, M is —CO(CH$_2$)$_5$NH— or —CO(CH$_2$)$_5$NHCO(CH$_2$)$_5$NH—, wherein m is 1 or 0.

The method of nucleic acid detection using the nucleic acid derivative involves the incubation of the derivative with a probe. In one embodiment, the probe is attached to a glass chip.

In one embodiment, the nucleic acid labeling compounds attached to the nucleic acid have the following structures:

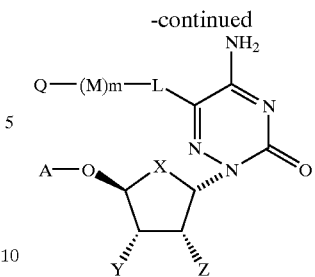

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —CH=CH(CH$_2$)$_n$NH—, wherein n is an integer ranging from about 1 to about 10; Q is biotin or carboxyfluorescein; and, M is —CO(CH$_2$)$_5$NH— or —CO(CH$_2$)$_5$NHCO(CH$_2$)$_5$NH—, wherein m is 1 or 0.

The method of nucleic acid detection using the nucleic acid derivative involves the incubation of the derivative with a probe. In one embodiment, the probe is attached to a glass chip.

In one embodiment, the nucleic acid labeling compounds attached to the nucleic acid have the following structures:

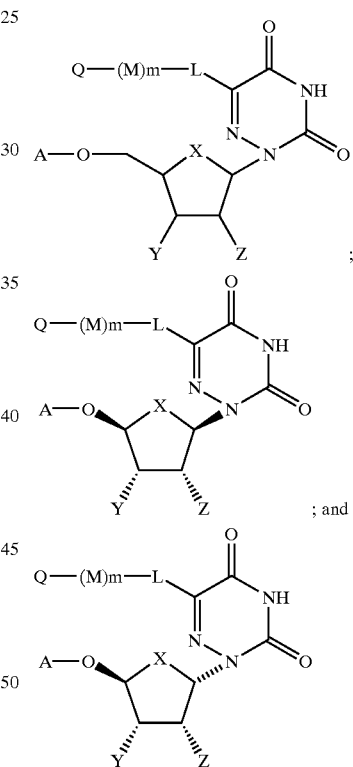

wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —CH=CH(CH$_2$)$_n$NH—, wherein n is an integer ranging from about 1 to about 10; Q is biotin or carboxyfluorescein; and, M is —CO(CH$_2$)$_5$NH— or —CO(CH$_2$)$_5$NHCO(CH$_2$)$_5$NH—, wherein m is 1 or 0.

The method of nucleic acid detection using the nucleic acid derivative involves the incubation of the derivative with a probe. In one embodiment, the probe is attached to a glass chip.

BEST MODE FOR CARRYING OUT THE INVENTION

Definitions

Figure 1:
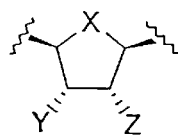
FIG. 1 shows a nonlimiting set of template moieties.
Figure 1:
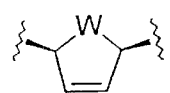
Figure 1:
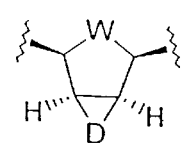
Figure 1:
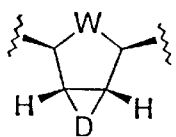
Figure 1:
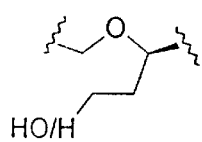
Figure 1:
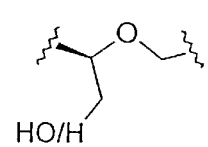
Figure 1:
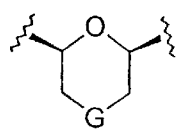
Figure 1:
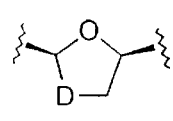
Figure 1:
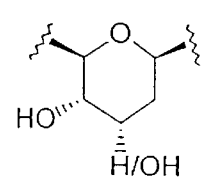
Figure 1:
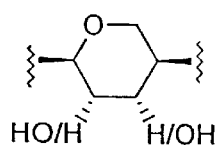
Figure 1:
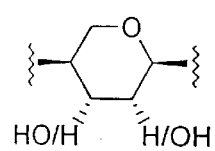
Figure 1:
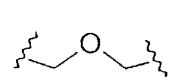
Figure 1:
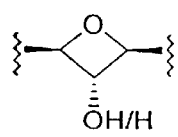
Figure 1:
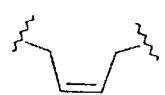
Figure 1:
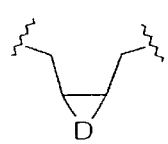

"Alkyl" refers to a straight chain, branched or cyclic chemical group containing only carbon and hydrogen. Alkyl groups include, without limitation, ethyl, propyl, butyl, pentyl, cyclopentyl and 2-methylbutyl. Alkyl groups are unsubstituted or substituted with 1 or more substituents (e.g., halogen, alkoxy, amino).

"Aryl" refers to a monovalent, unsaturated aromatic carbocyclic group. Aryl groups include, without limitation, phenyl, naphthyl, anthryl and biphenyl. Aryl groups are unsubstituted or substituted with 1 or more substituents (e.g. halogen, alkoxy, amino).

"Amido alkyl" refers to a chemical group having the structure —C(O)NR$_3$R$_4$—, wherein R$_3$ is hydrogen, alkyl or aryl, and R$_4$ is alkyl or aryl. Preferably, the amido alkyl group is of the structure —C(O)NH(CH$_2$)$_n$R$_5$—, wherein n is an integer ranging from about 2 to about 10, and R$_5$ is O, NR$_6$, or C(O), and wherein R$_6$ is hydrogen, alkyl or aryl. More preferably, the amido alkyl group is of the structure —C(O)NH(CH$_2$)$_n$N(H)—, wherein n is an integer ranging from about 2 to about 6. Most preferably, the amido alkyl group is of the structure —C(O)NH(CH$_2$)$_4$N(H)—.

"Alkynyl alkyl" refers to a chemical group having the structure —C≡C—R$_4$—, wherein R$_4$ is alkyl or aryl. Preferably, the alkynyl alkyl group is of the structure —C≡C—(CH$_2$)$_n$R$_5$—, wherein n is an integer ranging from 1 to about 10, and R$_5$ is O, NR$_6$ or C(O), wherein R$_6$ is hydrogen, alkyl or aryl. More preferably, the alkynyl alkyl group is of the structure —C≡C—(CH$_2$)$_n$N(H)—, wherein n is an integer ranging from 1 to about 4. Most preferably, the alkynyl alkyl group is of the structure —C≡C—CH$_2$N(H)—.

"Alkenyl alkyl" refers to a chemical group having the structure —CH=CH—R$_4$—, wherein R$_4$ is alkyl or aryl. Preferably, the alkenyl alkyl group is of the structure —CH=CH—(CH$_2$)$_n$R$_5$—, wherein n is an integer ranging from 1 to about 10, and R$_5$ is O, NR$_6$ or C(O), wherein R$_6$ is hydrogen, alkyl or aryl. More preferably, the alkenyl alkyl group is of the structure —CH=CH—(CH$_2$)$_n$N(H)—, wherein n is an integer ranging from 1 to about 4. Most preferably, the alkenyl alkyl group is of the structure —CH=CH—CH$_2$N(H)—.

"Functionalized alkyl" refers to a chemical group of the structure —(CH$_2$)$_n$R$_7$—, wherein n is an integer ranging from 1 to about 10, and R$_7$ is O, S, NH or C(O). Preferably, the functionalized alkyl group is of the structure —(CH$_2$)$_n$C(O)—, wherein n is an integer ranging from 1 to about 4. More preferably, the functionalized alkyl group is of the structure —CH$_2$C(O)—.

"Alkoxy" refers to a chemical group of the structure —O(CH$_2$)$_n$R$_8$—, wherein n is an integer ranging from 2 to about 10, and R$_8$ is O, S, NH or C(O). Preferably, the alkoxy group is of the structure —O(CH$_2$)$_n$C(O)—, wherein n is an integer ranging from 2 to about 4. More preferably, the alkoxy group is of the structure —OCH$_2$CH$_2$C(O)—.

"Thio" refers to a chemical group of the structure —S(CH$_2$)$_n$R$_8$—, wherein n is an integer ranging from 2 to about 10, and R$_8$ is O, S, NH or C(O). Preferably, the thio group is of the structure —S(CH$_2$)$_n$C(O)—, wherein n is an integer ranging from 2 to about 4. More preferably, the thio group is of the structure —SCH$_2$CH$_2$C(O)—.

"Amino alkyl" refers to a chemical group having an amino group attached to an alkyl group. Preferably an amino alkyl is of the structure —NH(CH$_2$)$_n$NH—, wherein n is an integer ranging from about 2 to about 10. More preferably it is of the structure —NH(CH$_2$)$_n$NH—, wherein n is an integer ranging from about 2 to about 4. Most preferably, the amino alkyl group is of the structure —NH(CH$_2$)$_4$NH—.

"Nucleic acid" refers to a polymer comprising 2 or more nucleotides and includes single-, double- and triple stranded polymers. "Nucleotide" refers to both naturally occurring and non-naturally occurring compounds and comprises a heterocyclic base, a sugar, and a linking group, preferably a phosphate ester. For example, structural groups may be added to the ribosyl or deoxyribosyl unit of the nucleotide, such as a methyl or allyl group at the 2'-O position or a fluoro group that substitutes for the 2'-O group. The linking group, such as a phosphodiester, of the nucleic acid may be substituted or modified, for example with methyl phosphonates or O-methyl phosphates. Bases and sugars can also be modified, as is known in the art. "Nucleic acid," for the purposes of this disclosure, also includes "peptide nucleic acids" in which native or modified nucleic acid bases are attached to a polyamide backbone.

"Probe" refers to a nucleic acid that can be used to detect, by hybridization, a target nucleic acid. Preferably, the probe is complementary to the target nucleic acid along the entire length of the probe, but hybridization can occur in the presence of one or more base mismatches between probe and target.

Nucleic Acid Labeling Compounds

The nucleic acid labeling compounds of the present invention are of the following structure:

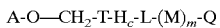

wherein A is hydrogen or a functional group that permits the attachment of the nucleic acid labeling compound to a nucleic acid; T is a template moiety; $H_c$ is a heterocyclic group; L is a linker moiety; Q is a detectable moiety; and M is an connecting group, wherein m is an integer ranging from 0 to about 5.

The group A is either hydrogen or a functional group that permits the attachment of a nucleic acid labeling compound to a nucleic acid. Nonlimiting examples of such groups include the following: monophosphate; diphosphate; triphosphate ($H_4O_9P$); phosphoramidite (($R_2N$)(R'O)P), wherein R is linear, branched or cyclic alkyl, and R' is a protecting group such as 2-cyanoethyl; and H-phosphonate (HP(O)O—HNR$_3$), wherein R is linear, branched or cyclic alkyl.

The template moiety (T) is covalently attached to a methylene group ($CH_2$) at one position and a heterocyclic group ($H_c$) at another position. A nonlimiting set of template moieties is shown in FIG. 1, wherein the substituents are defined as follows: X is O, S, $NR_1$ or $CHR_2$; Y is H, $N_3$, F, $OR_9$, $SR_9$ or $NHR_9$; Z is H, $N_3$, F or $OR_{10}$; W is O, S or $CH_2$; D is O or S; and, G is O, NH or $CH_2$. The substituents $R_1$, $R_2$, $R_9$ and $R_{10}$ are independent of one another and are H, alkyl or aryl.

Figure 2:
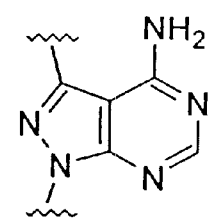
FIG. 2 shows a nonlimiting set of heterocyclic groups: 4-aminopyrazolo[3,4-d]pyrimidine, pyrazolo[3,4-d]pyrimidine, 1,3-diazole (imidazole), 1,2,4-triazine-3-one, 1,2,4-triazine-3,5-dione and 5-amino-1,2,4-triazine-3-one.
Figure 2:
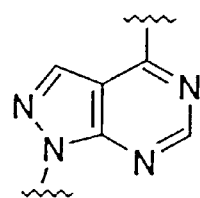
Figure 2:
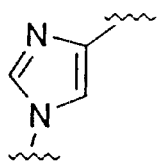
Figure 2:
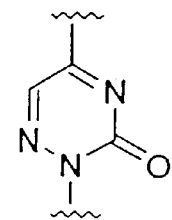
Figure 2:
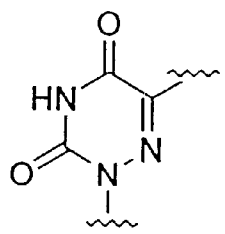
Figure 2:
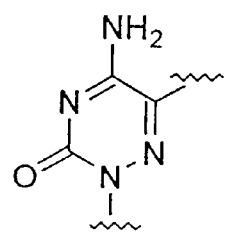

The heterocyclic group ($H_c$) is a cyclic moiety containing both carbon and a heteroatom. Nonlimiting examples of heterocyclic groups contemplated by the present invention are shown in FIG. 2.: 4-aminopyrazolo[3,4-d]pyrimidine; pyrazolo[3,4-d]pyrimidine; 1,3-diazole (imidazole); 1,2,4-triazine-3-one; 1,2,4-triazine-3,5-dione; and, 5-amino-1,2,4-triazine-3-one.

The linker moiety (L) of the nucleic acid labeling compound is covalently bound to the heterocycle ($H_c$) at one terminal position. It is attached to the detectable moiety (Q) at another terminal position, either directly or through a connecting group (M). It is of a structure that is sterically and electronically suitable for incorporation into a nucleic acid. Nonlimiting examples of linker moieties include amido alkyl groups, alkynyl alkyl groups, alkenyl alkyl groups, functionalized alkyl groups, alkoxyl groups, thio groups and amino alkyl groups.

Amido alkyl groups are of the structure —C(O)NR$_3$R$_4$—, wherein $R_3$ is hydrogen, alkyl or aryl, and $R_4$ is alkyl or aryl. The amido alkyl group is preferably of the structure —C(O)NH(CH$_2$)$_n$R$_5$—, wherein n is an integer ranging from about 2 to about 10 and $R_5$ is O, $NR_6$ or C(O), and wherein $R_6$ is hydrogen, alkyl or aryl. More preferably, the amido alkyl group is of the structure —C(O)NH(CH$_2$)$_n$N(H)—, wherein n is an integer ranging from about 2 to about 6. Most preferably, the amido alkyl group is of the structure —C(O)NH(CH$_2$)$_4$N(H)—.

Alkynyl alkyl groups are of the structure —C≡C—R$_4$—, wherein $R_4$ is alkyl or aryl. The alkynyl alkyl group is preferably of the structure —C≡C(CH$_2$)$_n$R$_5$—, wherein n is an integer ranging from 1 to about 10 and $R_5$ is O, $NR_6$ or C(O), and wherein $R_6$ is hydrogen, alkyl or aryl. More preferably, the alkynyl alkyl group is of the structure —C≡C—(CH$_2$)$_n$N(H)—, wherein n is an integer ranging from 1 to about 4. Most preferably, the alkynyl alkyl group is of the structure —C≡C—CH$_2$N(H)—.

Alkenyl alkyl groups are of the structure —CH=CH—R$_4$—, wherein $R_4$ is alkyl or aryl. The alkenyl alkyl group is preferably of the structure —CH=CH(CH$_2$)$_n$R$_5$—, wherein n is an integer ranging from 1 to about 10, and $R_5$ is O, $NR_6$ or C(O), and wherein $R_6$ is hydrogen, alkyl or aryl. More preferably, the alkenyl alkyl group is of the structure —CH=CH(CH$_2$)$_n$NH—, wherein n is an integer ranging from 1 to about 4. Most preferably, the alkenyl alkyl group is of the structure —CH=CHCH$_2$NH—.

Functionalized alkyl groups are of the structure —(CH$_2$)$_n$R$_7$—, wherein n is an integer ranging from 1 to about 10, and $R_7$ is O, S, NH, or C(O). The functionalized alkyl group is preferably of the structure —(CH$_2$)$_n$C(O)—, wherein n is an integer ranging from 1 to about 4. More preferably, the functionalized alkyl group is —CH$_2$C(O)—.

Alkoxy groups are of the structure —O(CH$_2$)$_n$R$_8$—, wherein n is an integer ranging from 2 to about 10, and $R_8$ is O, S, NH, or C(O). The alkoxy group is preferably of the structure —O(CH$_2$)$_n$C(O)—, wherein n is an integer ranging from 2 to about 4. More preferably, the alkoxy group is of the structure —OCH$_2$CH$_2$C(O)—.

Thio groups are of the structure —S(CH$_2$)$_n$R$_8$—, wherein n is an integer ranging from 2 to about 10, and $R_8$ is O, S, NH, or C(O). The thio group is preferably of the structure —S(CH$_2$)$_n$C(O)—, wherein n is an integer ranging from 2 to about 4. More preferably, the thio group is of the structure —SCH$_2$CH$_2$C(O)—.

Amino alkyl groups comprise an amino group attached to an alkyl group. Preferably, amino alkyl groups are of the structure —NH(CH$_2$)$_n$NH—, wherein n is an integer ranging from about 2 to about 10. The amino alkyl group is more preferably of the structure —NH(CH$_2$)$_n$NH—, wherein n is an integer ranging from about 2 to about 4. Most preferably, the amino alkyl group is of the structure —NH(CH$_2$)$_4$NH—.

The detectable moiety (Q) is a chemical group that provides an signal. The signal is detectable by any suitable means, including spectroscopic, photochemical, biochemical, immunochemical, electrical, optical or chemical means. In certain cases, the signal is detectable by 2 or more means.

The detectable moiety provides the signal either directly or indirectly. A direct signal is produced where the labeling group spontaneously emits a signal, or generates a signal upon the introduction of a suitable stimulus. Radiolabels, such as $^3H$, $^{125}I$, $^{35}S$, $^{14}C$ or $^{32}P$, and magnetic particles, such as Dynabeads™, are nonlimiting examples of groups that directly and spontaneously provide a signal. Labeling groups that directly provide a signal in the presence of a stimulus include the following nonlimiting examples: colloidal gold (40–80 nm diameter), which scatters green light with high efficiency; fluorescent labels, such as fluorescein, texas red, rhodamine, and green fluorescent protein (Molecular Probes, Eugene, Oreg.), which absorb and subsequently emit light; chemiluminescent or bioluminescent labels, such as luminol, lophine, acridine salts and luciferins, which are electronically excited as the result of a chemical or biological reaction and subsequently emit light; spin labels, such as vanadium, copper, iron, manganese and nitroxide free radicals, which are detected by electron spin resonance (ESR) spectroscopy; dyes, such as quinoline dyes, triarylmethane dyes and acridine dyes, which absorb specific wavelengths of light; and colored glass or plastic (e.g., polystyrene, polypropylene, latex, etc.) beads. See U.S. Pat. Nos. 3,817,837; 3,850,752; 3,939,350; 3,996,345; 4,277, 437; 4,275,149 and 4,366,241.

A detectable moiety provides an indirect signal where it interacts with a second compound that spontaneously emits a signal, or generates a signal upon the introduction of a suitable stimulus. Biotin, for example, produces a signal by forming a conjugate with streptavidin, which is then detected. See Hybridization With Nucleic Acid Probes. In *Laboratory Techniques in Biochemistry and Molecular Biology;* Tijssen, P., Ed.; Elsevier: New York, 1993; Vol.24. An enzyme, such as horseradish peroxidase or alkaline phosphatase, that is attached to an antibody in a label-antibody-antibody as in an ELISA assay, also produces an indirect signal.

A preferred detectable moiety is a fluorescent group. Flourescent groups typically produce a high signal to noise ratio, thereby providing increased resolution and sensitivity in a detection procedure. Preferably, the fluorescent group absorbs light with a wavelength above about 300 nm, more preferably above about 350 nm, and most preferably above about 400 nm. The wavelength of the light emitted by the fluorescent group is preferably above about 310 nm, more preferably above about 360 nm, and most preferably above about 410 nm.

The fluorescent detectable moiety is selected from a variety of structural classes, including the following nonlimiting examples: 1- and 2-aminonaphthalene, p,p'diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salicylate, strophanthidin, porphyrins, triarylmethanes, flavin, xanthene dyes (e.g., fluorescein and rhodamine dyes); cyanine dyes; 4,4-difluoro-4-bora-3a,4a-diaza-s-indacene dyes and fluorescent proteins (e.g., green fluorescent protein, phycobiliprotein).

A number of fluorescent compounds are suitable for incorporation into the present invention. Nonlimiting examples of such compounds include the following: dansyl chloride; fluoresceins, such as 3,6-dihydroxy-9-phenylxanthhydrol; rhodamineisothiocyanate; N-phenyl-1-amino-8-sulfonatonaphthalene; N-phenyl-2-amino-6-sulfonatonaphthanlene; 4-acetamido-4-isothiocyanatostilbene-2,2'-disulfonic acid; pyrene-3-sulfonic acid; 2-toluidinonapthhalene-6-sulfonate; N-phenyl, N-methyl 2-aminonaphthalene-6'-sulfonate; ethidium bromide; stebrine; auromine-0,2-(9-anthroyl) palmitate; dansyl phosphatidylethanolamin; N,N'-dioctadecyl oxacarbocyanine; N,N'-dihexyl oxacarbocyanine; merocyanine, 4-(3'-pyrenyl)butryate; d-3-aminodesoxy-equilenin; 12-(9'-anthroyl)stearate; 2-methylanthracene; 9-vinylanthracene; 2,2'-(vinylene-p-phenylene)bisbenzoxazole; p-bis[2-(4-methyl-5-phenyl oxazolyl)]benzene; 6-dimethylamino-1,2-benzophenzin; retinol; bis(3'-aminopyridinium)-1,10-decandiyl diiodide; sulfonaphthylhydrazone of hellibrienin; chlorotetracycline; N-(7-dimethylamino-4-methyl-2-oxo-3-chromenyl) maleimide; N-[p-(2-benzimidazolyl)phenyl]maleimide; N-(4-fluoranthyl)maleimide; bis(homovanillic acid); resazarin; 4-chloro-7-nitro-2,1,3-benzooxadizole; merocyanine 540; resorufin; rose bengal and 2,4-diphenyl-3(2H)-furanone. Preferably, the fluorescent detectable moiety is a fluorescein or rhodamine dye.

Another preferred detectable moiety is colloidal gold. The colloidal gold particle is typically 40 to 80 nm in diameter. The colloidal gold may be attached to a labeling compound in a variety of ways. In one embodiment, the linker moiety of the nucleic acid labeling compound terminates in a thiol group (—SH), and the thiol group is directly bound to colloidal gold through a dative bond. See Mirkin et al. *Nature* 1996, 382, 607–609. In another embodiment, it is attached indirectly, for instance through the interaction between colloidal gold conjugates of antibiotin and a biotinylated labeling compound. The detection of the gold labeled compound may be enhanced through the use of a silver enhancement method. See Danscher et al. *J. Histotech* 1993, 16, 201–207.

The connecting group $(M)_m$ may serve to covalently attach the linker group (L) to the detectable moiety (Q). It is of any suitable structure that will not interfere with the function of the labeling compound. Nonlimiting examples of M groups include the following: —CO(CH$_2$)$_5$NH—, —CO—, —CO(O)—, —CO(NH)—, and —CO(CH$_2$)$_5$NHCO(CH$_2$)$_5$NH—; wherein, m is an integer ranging from 0 to about 5, preferably 0 to about 3.

In one embodiment, the nucleic acid labeling compounds of the present invention are of the following structure:

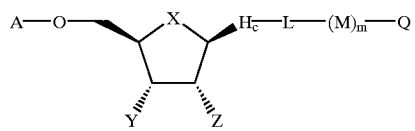

wherein L is a linker moiety; Q is a detectable moiety; X is O, S, NR$_1$ or CHR$_2$; Y is H, N$_3$, F, OR$_9$, SR$_9$ or NHR$_9$; Z is H, N$_3$, F or OR$_{10}$; H$_c$ is a heterocyclic group; A is H or a functional group that permits the attachment of the nucleic acid label to a nucleic acid; and, M is a connecting group, wherein m is an integer ranging from 0 to about 3. The substituents R$_1$, R$_2$, R$_9$ and R$_{10}$ are independent of one another and are H, alkyl or aryl.

In one embodiment, the heterocyclic group (H$_c$) is an imidazole, and the nucleic acid labeling compounds have the following structures:

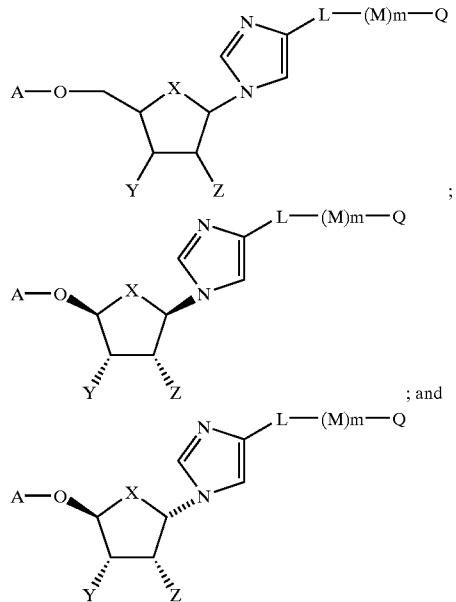

wherein L is a linker moiety; Q is a detectable moiety; X is O, S, NR$_1$ or CHR$_2$; Y is H, N$_3$, F, OR$_9$, SR$_9$ or NHR$_9$; Z is H, N$_3$, F or OR$_{10}$; A is H or a functional group that permits the attachment of the nucleic acid label to a nucleic acid; and, M is a connecting group, wherein m is an integer ranging from 0 to about 3. The substituents R$_1$, R$_2$, R$_9$ and R$_{10}$ are independent of one another and are H, alkyl or aryl.

In a preferred embodiment, the heterocyclic group (H$_c$) is an imidazole and the linking moiety is amido alkyl:

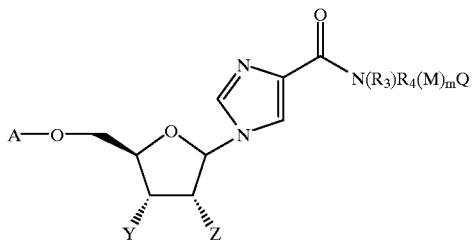

wherein Y is hydrogen or hydroxyl; Z is hydrogen or hydroxyl; $R_3$ is hydrogen or alkyl; $R_4$ is —$(CH_2)_nNH$—, wherein n is an integer ranging from about 2 to about 10; Q is biotin or carboxyfluorescein; A is hydrogen or $H_4O_9P_3$—; and, M is —$CO(CH_2)_5NH$— or —CO—, wherein m is 1 or 0. More preferably, Y and Z are hydrogen; $R_3$ is hydrogen; $R_4$ is —$(CH_2)_4NH$—; A is $H_4O_9P_3$—; and, Q is biotin, wherein M is —$CO(CH_2)_5NH$— and m is 1, or 5- or 6-carboxyfluorescein, wherein m is 0.

In another embodiment, the heterocyclic group ($H_c$) is a C3 substituted 4-amino-pyrazolo[3,4-d]pyrimidine, and the nucleic acid labeling compounds have the following structures:

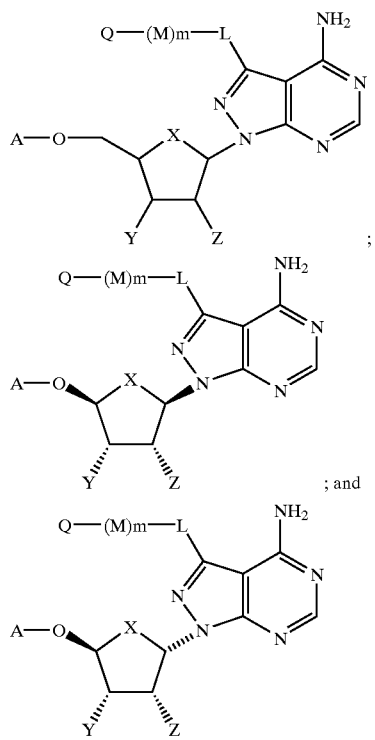

wherein L is a linker moiety; Q is a detectable moiety; X is O, S, $NR_1$ or $CHR_2$; Y is H, $N_3$, F, $OR_9$, $SR_9$ or $NHR_9$; Z is H, $N_3$, F or $OR_{10}$; A is H or a functional group that permits the attachment of the nucleic acid label to a nucleic acid; and, M is a connecting group, wherein m is an integer ranging from 0 to about 3. The substituents $R_1$, $R_2$, $R_9$ and $R_{10}$ are independent of one another and are H, alkyl or aryl.

In a preferred embodiment, the heterocyclic group ($H_c$) is a C3 substituted 4-aminopyrazolo[3,4-d]pyrimidine and the linking group is an alkynyl alkyl:

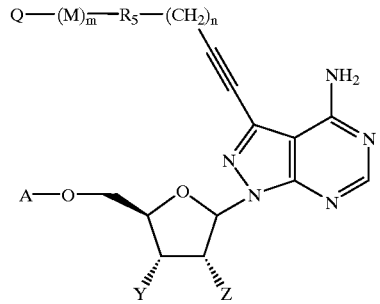

wherein Y is hydrogen or hydroxyl; Z is hydrogen or hydroxyl; n is an integer ranging from 1 to about 10; $R_5$ is O or NH; A is hydrogen or $H_4O_9P_3$—; Q is biotin or carboxyfluorescein; M is —$CO(CH_2)_5NH$—, wherein m is 1 or 0. More preferably, Y and Z are OH; n is 1; $R_5$ is NH; A is $H_4O_9P_3$—; and, Q is biotin or 5- or 6-carboxyfluorescein, wherein m is 1.

In another embodiment, the heterocyclic group ($H_c$) is an C4 substituted pyrazolo[3,4-d]pyrimidine, and the nucleic acid labeling compounds have the following structures:

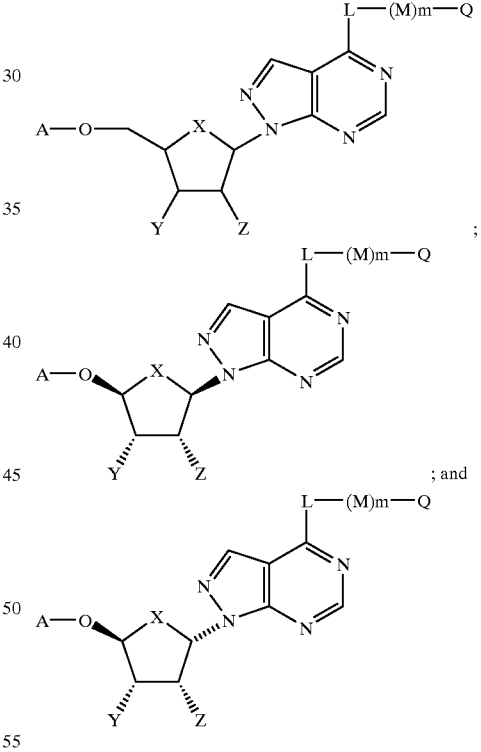

wherein L is a linker moiety; Q is a detectable moiety; X is O, S, $NR_1$ or $CHR_2$; Y is H, $N_3$, F, $OR_9$, $SR_9$ or $NHR_9$; Z is H, $N_3$, F or $OR_{10}$; A is H or a functional group that permits the attachment of the nucleic acid label to a nucleic acid; and, M is a connecting group, wherein m is an integer ranging from 0 to about 3. The substituents $R_1$, $R_2$, $R_9$ and $R_{10}$ are independent of one another and are H, alkyl or aryl.

In a preferred embodiment, the heterocyclic group ($H_c$) is an N4 substituted 4-amino-pyrazolo[3,4-d]pyrimidine and the linking group is an amino alkyl:

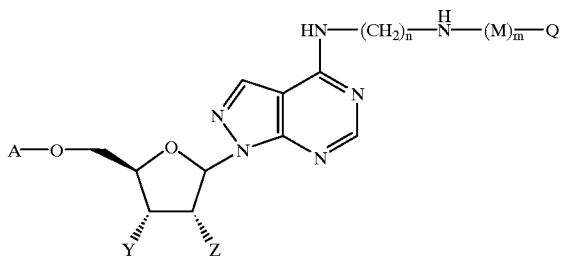

wherein Y is hydrogen or hydroxyl; Z is hydrogen or hydroxyl; n is an integer ranging from about 2 to about 10; A is hydrogen or $H_4O_9P_3$—; Q is biotin or carboxyfluorescein; M is —$CO(CH_2)_5NH$— or —$CO(CH_2)_5NHCO(CH_2)_5NH$—, wherein m is 1 or 0. More preferably, Y and Z are hydrogen; n is 4; A is $H_4O_9P_3$—; Q is biotin or 5- or 6-carboxyfluorescein, wherein m is 0.

In another embodiment, the heterocyclic group ($H_c$) is a 1,2,4-triazine-3-one, and the nucleic acid labeling compounds have the following structures:

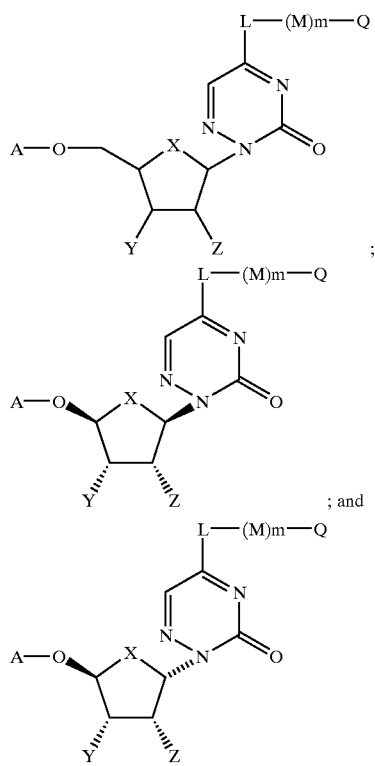

wherein L is a linker moiety; Q is a detectable moiety; X is O, S, $NR_1$ or $CHR_2$; Y is H, $N_3$, F, $OR_9$, $SR_9$ or $NHR_9$; Z is H, $N_3$, F or $OR_{10}$; A is H or a functional group that permits the attachment of the nucleic acid label to a nucleic acid; and, M is a connecting group, wherein m is an integer ranging from 0 to about 3. The substituents $R_1$, $R_2$, $R_9$ and $R_{10}$ are independent of one another and are H, alkyl or aryl.

In a preferred embodiment, the heterocyclic group ($H_c$) is a 1,2,4-triazine-3-one and the linking group is amino alkyl:

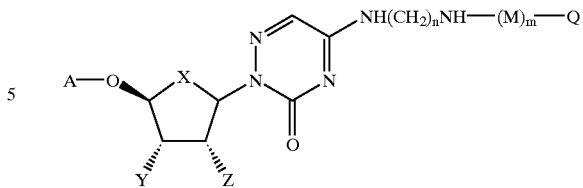

wherein Y is hydrogen or hydroxyl; Z is hydrogen or hydroxyl; n is an integer ranging from about 2 to about 10; A is hydrogen or $H_4O_9P_3$—; Q is biotin or carboxyfluorescein; M is —$CO(CH_2)_5NH$— or —$CO(CH_2)_5NHCO(CH_2)_5NH$—, wherein m is 1 or 0. More preferably, Y and Z are hydroxyl; n is 4; A is $H_4O_9P_3$—; Q is biotin or 5- or 6-carboxyfluorescein, wherein M is —$CO(CH_2)_5NH$—, and m is 1.

In another embodiment, the heterocyclic group ($H_c$) is a 1,2,4-triazine-3,5-dione, and the nucleic acid labeling compounds have the following structures:

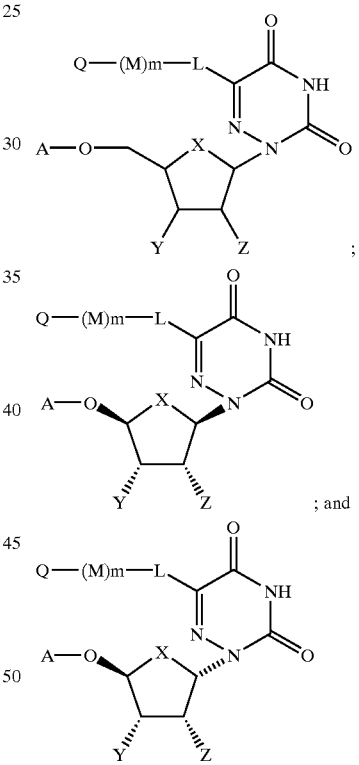

wherein L is a linker moiety; Q is a detectable moiety; X is O, S, $NR_1$ or $CHR_2$; Y is H, $N_3$, F, $OR_9$, $SR_9$ or $NHR_9$; Z is H, $N_3$, F or $OR_{10}$; A is H or a functional group that permits the attachment of the nucleic acid label to a nucleic acid; and, M is a connecting group, wherein m is an integer ranging from 0 to about 3. The substituents $R_1$, $R_2$, $R_9$ and $R_{10}$ are independent of one another and are H, alkyl or aryl.

In a preferred embodiment, the heterocyclic group ($H_c$) is a 1,2,4-triazine-3,5-dione and the linking group is alkenyl alkyl:

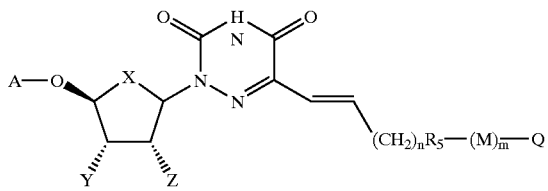

wherein Y is hydrogen or hydroxyl; Z is hydrogen or hydroxyl; n is an integer ranging from about 1 to about 10; $R_5$ is $NR_6$, wherein $R_6$ is hydrogen, alkyl or aryl; A is hydrogen or $H_4O_9P_3$—; Q is biotin or carboxyfluorescein; M is —$CO(CH_2)_5NH$— or —$CO(CH_2)_5NHCO(CH_2)_5NH$—, wherein m is 1 or 0.

In another embodiment, the heterocyclic group ($H_c$) is a 5-amino-1,2,4-triazine-3-one, and the nucleic acid labeling compounds have the following structures:

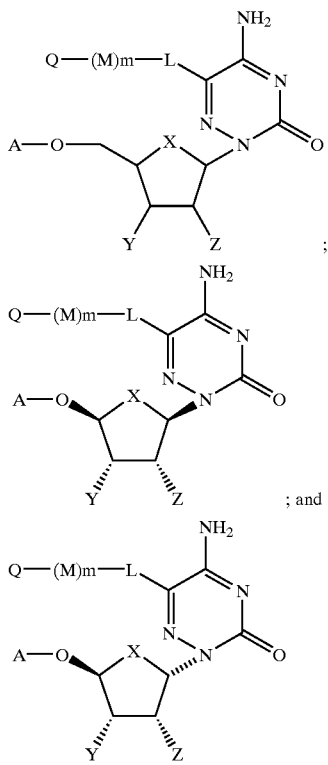

wherein L is a linker moiety; Q is a detectable moiety; X is O, S, $NR_1$ or $CHR_2$; Y is H, $N_3$, F, $OR_9$, $SR_9$ or $NHR_9$; Z is H, $N_3$, F or $OR_{10}$; A is H or a functional group that permits the attachment of the nucleic acid label to a nucleic acid; and, M is a connecting group, wherein m is an integer ranging from 0 to about 3. The substituents $R_1$, $R_2$, $R_9$ and $R_{10}$ are independent of one another and are H, alkyl or aryl.

In a preferred embodiment, the heterocyclic group ($H_c$) is a 5-amino-1,2,4-triazine-3-one and the linking group is alkenyl alkyl:

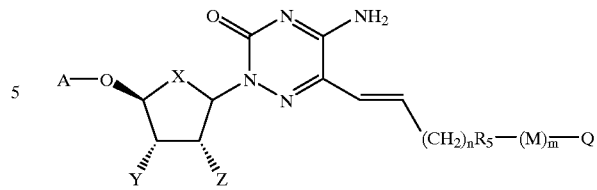

wherein Y is hydrogen or hydroxyl; Z is hydrogen or hydroxyl; n is an integer ranging from about 1 to about 10; $R_5$ is $NR_6$, wherein $R_6$ is hydrogen, alkyl or aryl; A is hydrogen or $H_4O_9P_3$—; Q is biotin or carboxyfluorescein; M is —$CO(CH_2)_5NH$— or —$CO(CH_2)_5NHCO(CH_2)_5NH$—, wherein m is 1 or 0.

Synthesis of Nucleic Acid Labeling Compounds

Figure 3:
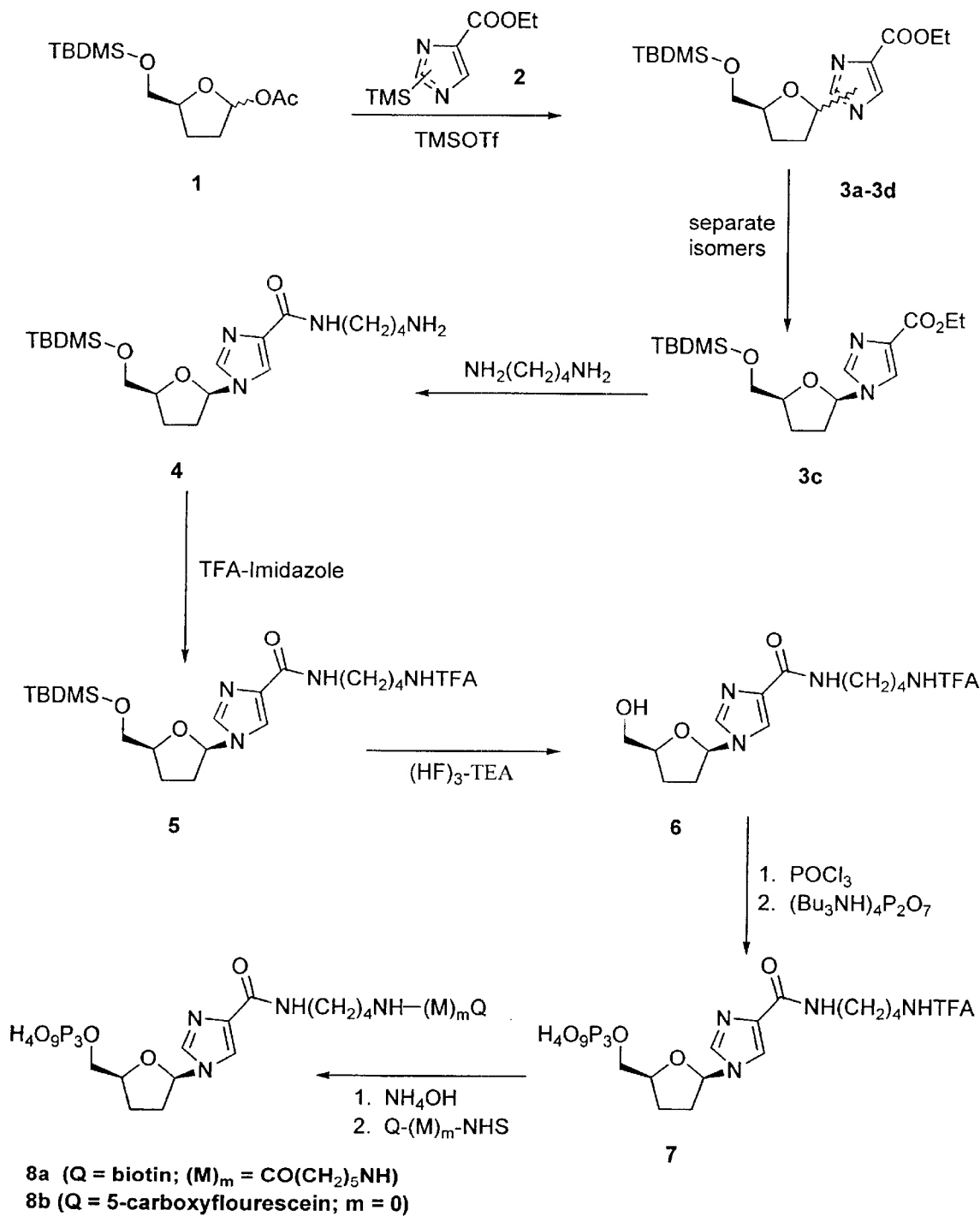
FIG. 3 shows a synthetic route to fluorescein and biotin labeled 1-(2,3-dideoxy-D-glycero-pentafuranosyl)imidazole-4-carboxamide nucleotides.

FIG. 3 shows a synthetic route to nucleic acid labeling compounds 8a and 8b, in which the heterocyclic group ($H_c$) is an imidazole and the linker moiety (L) is an amido alkyl. The silyl protected imidazole (2) was added to pentofuranose (1) to provide a mixture of carboethoxyimidazole dideoxyriboside isomers (3a–3d). The isomers were separated to afford purified 3c. The carboethoxy group of 3c was converted into an amino carboxamide (4) upon treatment with a diamine. The terminal amine of 4 was protected to give the trifluoroacetylated product 5. The silyl protecting group of 5 was removed, providing the primary alcohol 6. Compound 6 was converted into a 5'-triphosphate to afford 7. The trifluoroacetyl protecting group of 7 was removed, and the deprotected amine was reacted with biotin-$NH(CH_2)_5CO$—NHS or 5-carboxyfluorescein-NHS giving, respectively, nucleic acid labeling compounds 8a and 8b.

Figure 4:
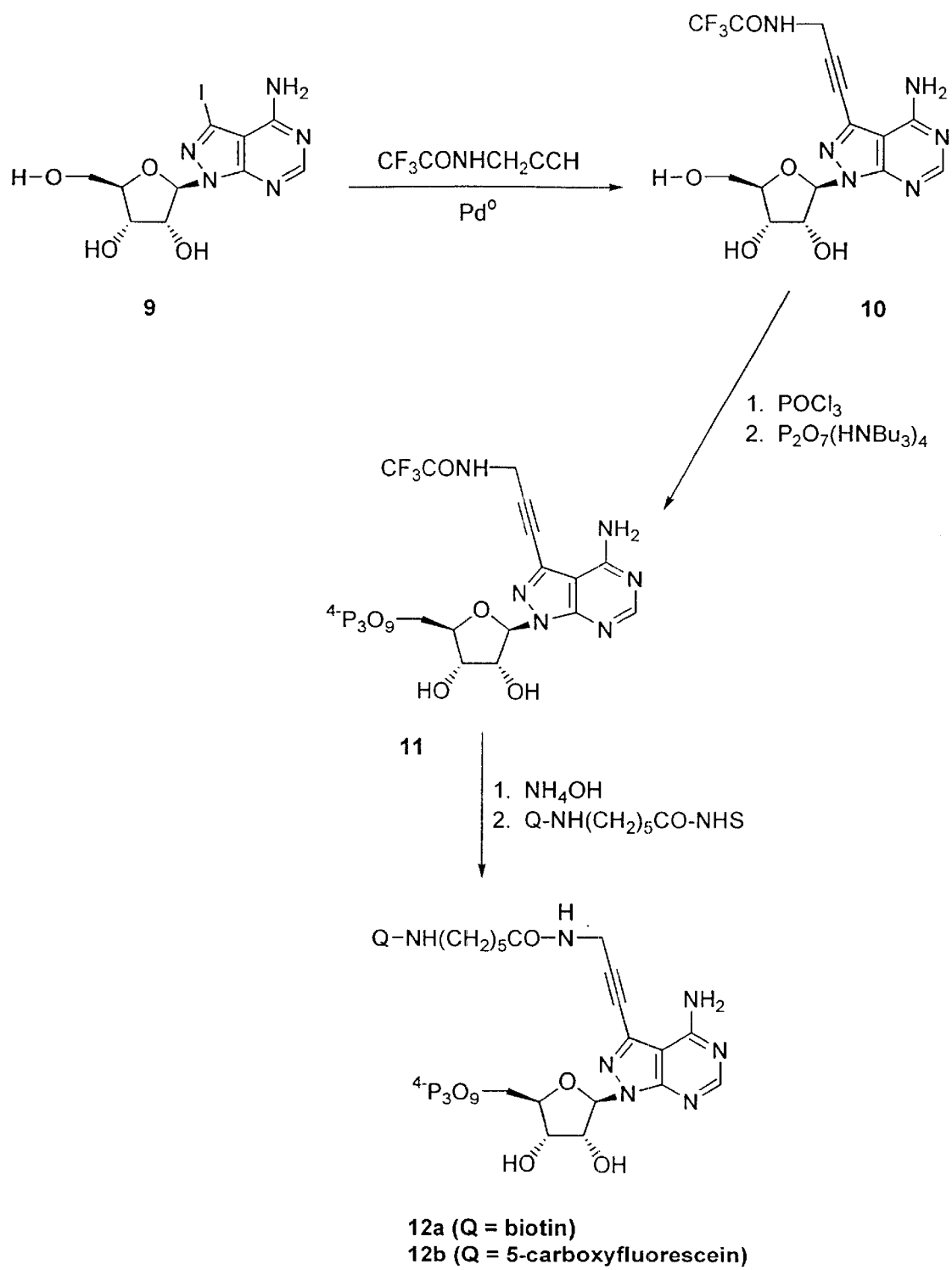
FIG. 4 shows a synthetic route to C3-labeled 4-aminopyrazolo[3,4-d]pyrimidine β-D-ribofuranoside triphosphates.

FIG. 4 shows a synthetic route to C3-labeled 4-aminopyrazolo[3,4-d]pyrimidine β-D-ribofuranoside triphosphates. A protected propargylamine linker was added to nucleoside (9) under palladium catalysis to provide the coupled product (10). The primary alcohol of the alkyne substituted nucleoside (10) was phosphorylated, yielding the 5'-triphosphate 11. The protected amine of triphosphate 11 was then deprotected, and the resulting primary amine was treated with a reactive biotin or fluorescein derivative to afford, respectively, nucleic acid labeling compounds 12a and 12b.

Figure 5:
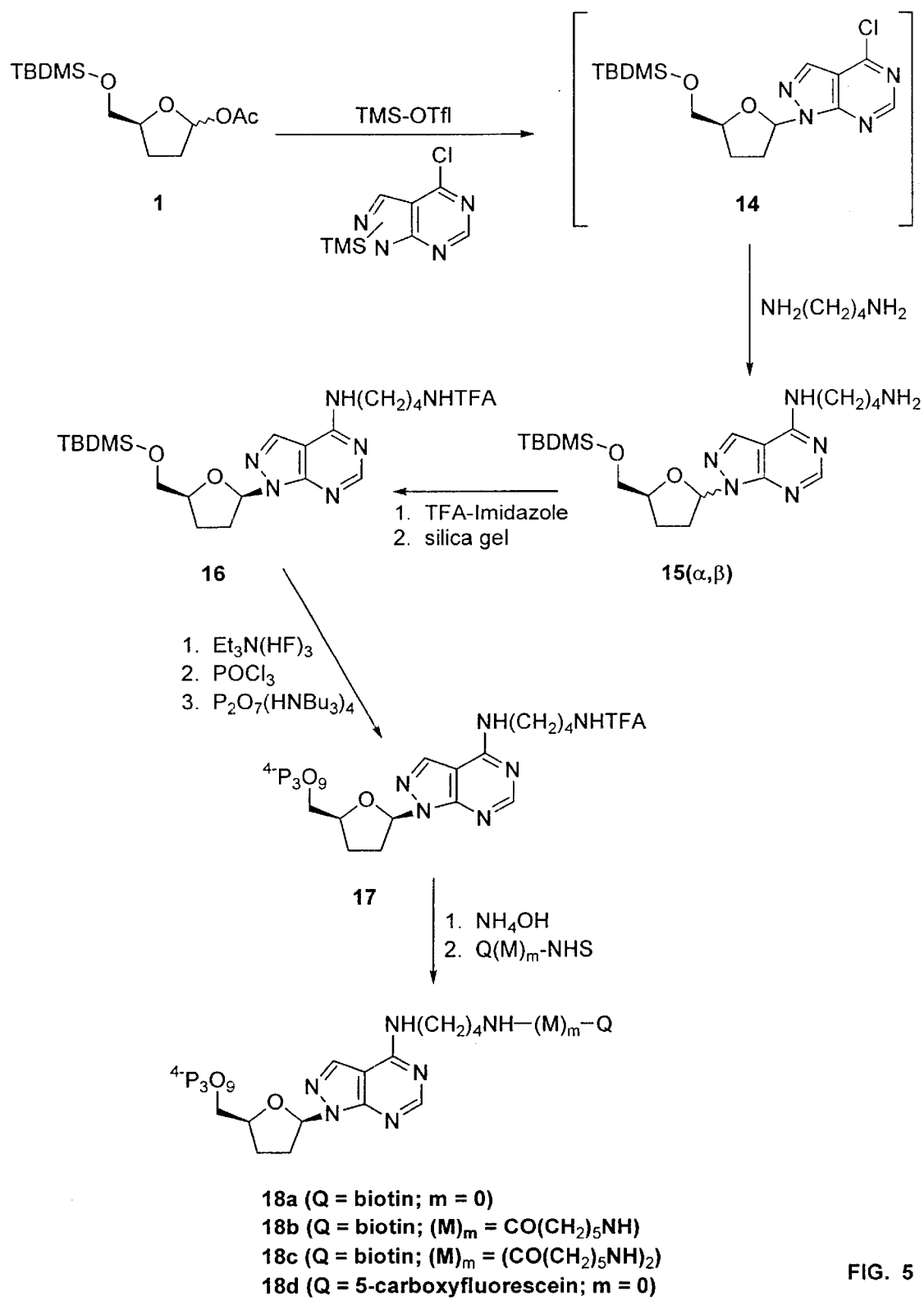
FIG. 5 shows a synthetic route to fluorescein and biotin labeled N6-dideoxy-pyrazolo[3,4-d]pyrimidine nucleotides.

FIG. 5 shows a synthetic route to pyrazolopyrimidine nucleotides. A chloropyrazolopyrimidine (13) was added to pentofuranose 1 to provide adduct 14 as a mixture of anomers. A diamine was added to compound 14, affording a mixture of primary amines (15). The primary amines (15) were protected and chromatographically separated to yield the pure β-anomer 16. The silyl group of 16 was removed and the resulting primary alcohol was phosphorylated to provide triphosphate 17. The trifluoroacetyl group of 17 was removed and the deprotected amine was treated with a reactive biotin or carboxyfluorescein derivative giving, respectively, nucleic acid labeling compounds 18a–18d.

Figure 6:
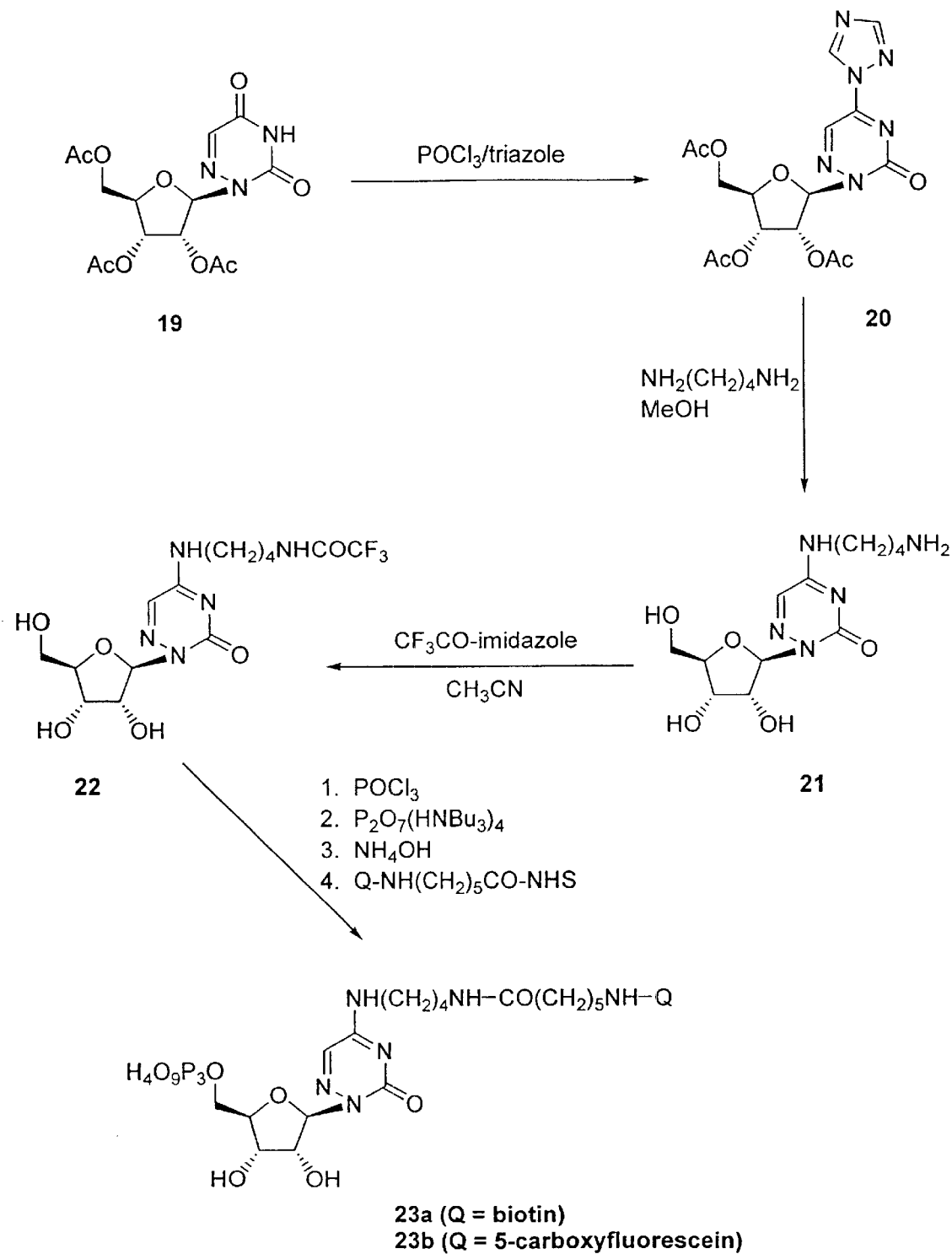
FIG. 6 shows a synthetic route to N4-labeled 1,2,4-triazine-3-one β-D-ribofuranoside triphosphates.

FIG. 6 shows a synthetic route to N4-labeled 1,2,4-triazine-3-one β-D-ribofuranoside triphosphates. 1,2,4-Triazine-3,5-dione ribonucleoside 19 was converted into the triazole nucleoside 20 upon treatment with triazole and phosphorous trichloride. Addition of a diamine to 20 provided aminoalkyl nucleoside 21. The primary amine of 21 was protected, affording trifluoroacetamide 22. The primary alcohol of 22 was phosphorylated, and the protected amine was deprotected and reacted with a reactive biotin or carboxyfluorescein derivative, giving, respectively, nucleic acid labeling compounds 23a and 23b.

Figure 7:
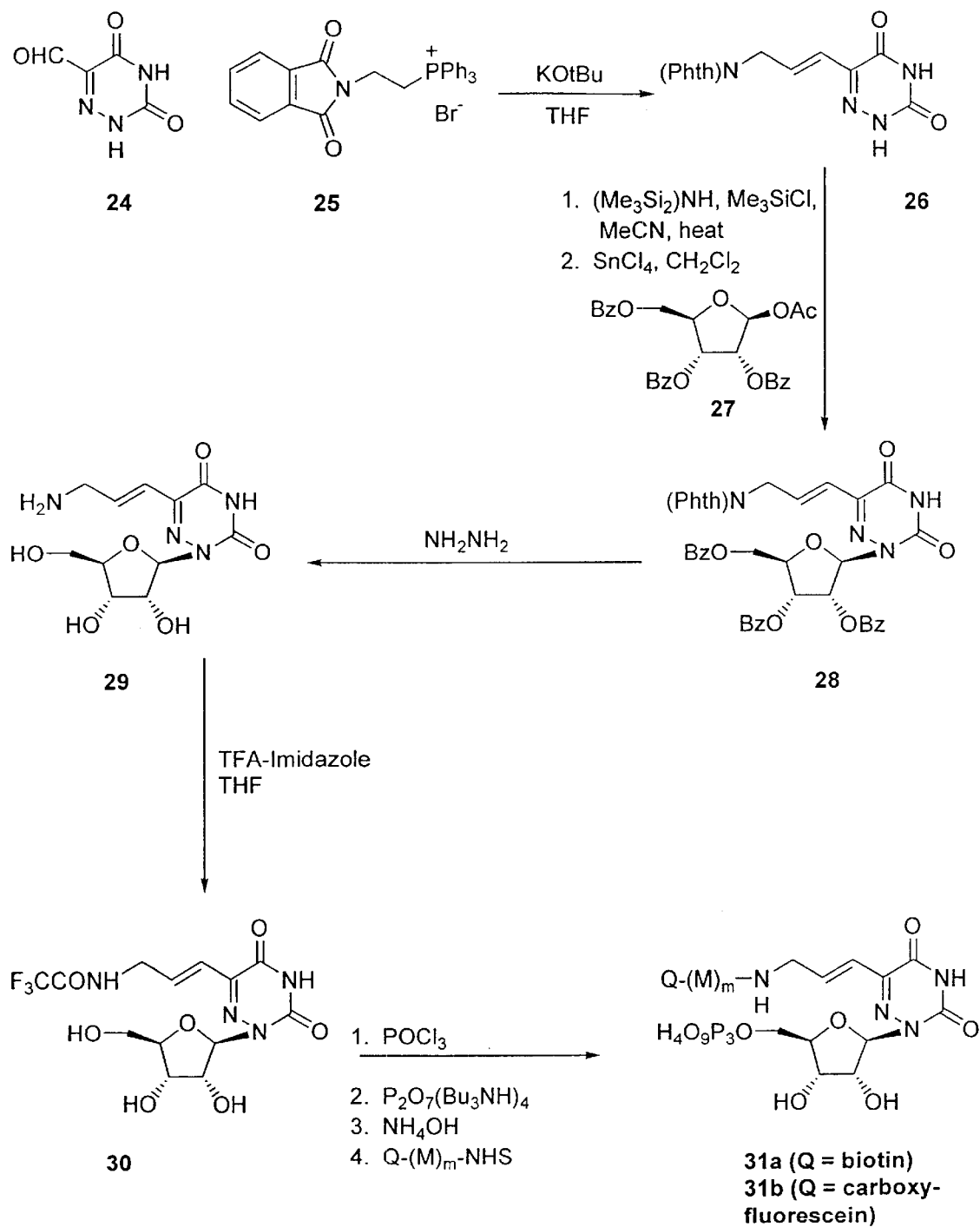
FIG. 7 shows a synthetic route to biotin and fluorescein C5-labeled 1,2,4-triazine-3,5-dione riboside triphosphates.

FIG. 7 shows a synthetic route to C5-labeled 1,2,4-triazine-3,5-dione riboside phosphates. Aldehyde 24 is reacted with ylide 25 to provide the phthalimide protected allylamine 26. Compound 26 is coupled with pentofuranoside 27, yielding nucleoside 28. The phthalimide group of 28 is removed upon treatment with hydrazine to afford primary amine 29. Amine 29 is protected as amide 30. Amide 30 is phosphorylated, deprotected and treated with a reactive derivative of biotin or carboxyfluorescein, giving, respectively, nucleic acid labeling compounds 31a and 31b.

Figure 8:
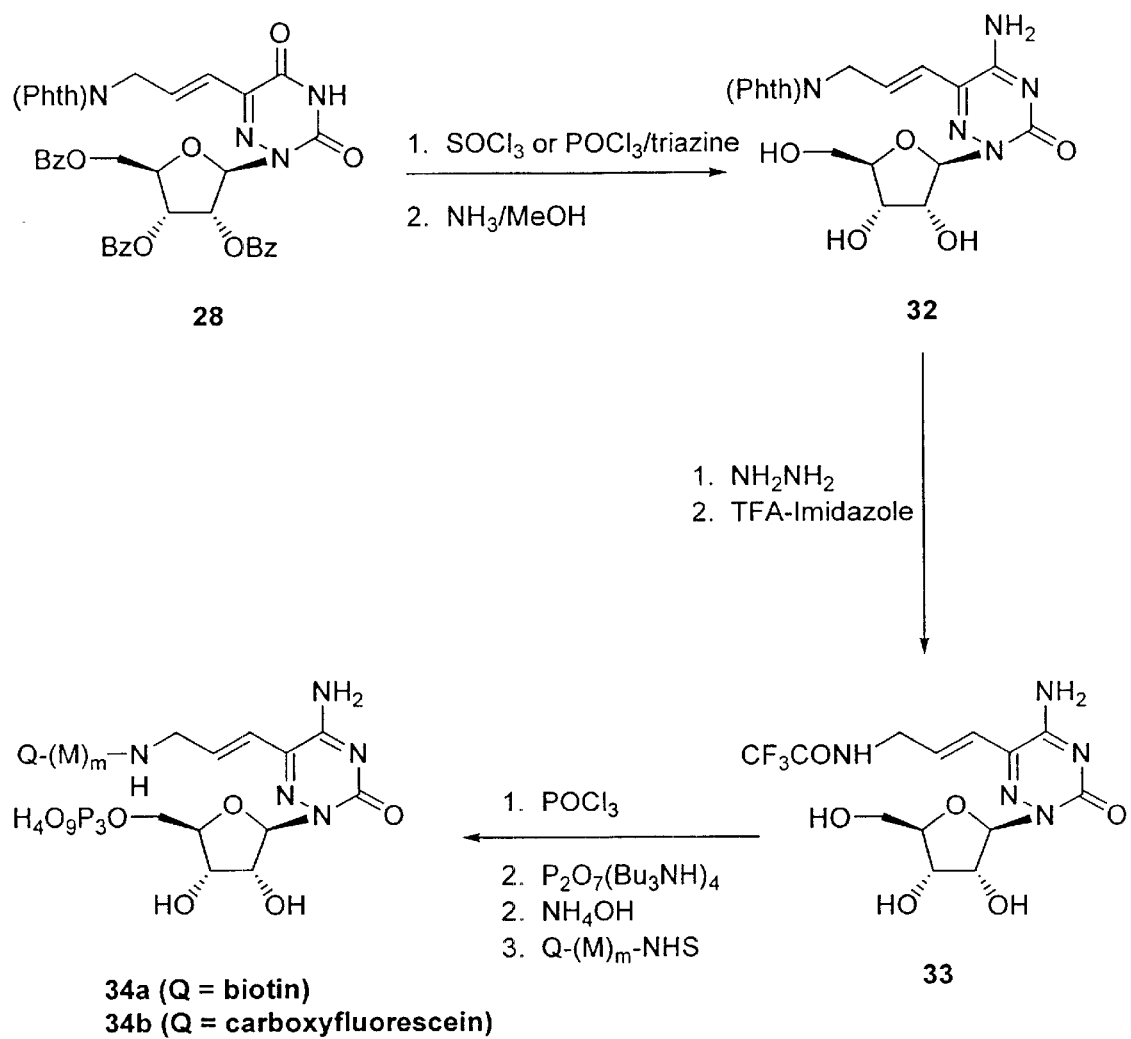
FIG. 8 shows a synthetic route to biotin and fluorescein C5-labeled 5-amino-1,2,4-triazine-3-one riboside triphosphates.

FIG. 8 shows a synthetic route to C5-labeled 5-amino-1, 2,4-triazine-3-one riboside triphosphates. Compound 28 is converted into the amino-1,3-6-triazine compound 32 upon treatment with a chlorinating agent and ammonia. The phthalimide group of 32 is removed upon treatment with hydrazine, and the resulting primary amine is protected to provide 33. Compound 33 is phosphorylated, deprotected and treated with a reactive derivative of biotin or carboxyfluorescein, giving, respectively, nucleic acid labeling compounds 34a and 34b.

Nucleic Acid Labeling

Nucleic acids can be isolated from a biological sample or synthesized, on a solid support or in solution for example, according to methods known to those of skill in the art. As used herein, there is no limitation on the length or source of the nucleic acid used in a labeling process. Exemplary methods of nucleic acid isolation and purification are described in Theory and Nucleic Acid Preparation. In *Laboratory Techniques in Biochemistry and Molecular Biology: Hybridization With Nucleic Acid Probes*; P. Tijssen, Ed.; Part I; Elsevier: N.Y., 1993. A preferred method of isolation involves an acid guanidinium-phenol-chloroform extraction followed by oligo dT column chromotography or (dT)n magnetic bead use. Sambrook et al. *Molecular Cloning: A Laboratory Manual*, 2nd ed.; Cold Spring Harbor Laboratory, 1989; Vols. 1–3; and *Current Protocols in Molecular Biology*; F. Ausubel et al. Eds.; Greene Publishing and Wiley Interscience: N.Y., 1987.

In certain cases, the nucleic acids are increased in quantity through amplification. Suitable amplification methods include, but are not limited to, the following examples: polymerase chain reaction (PCR) (Innis, et al. *PCR Protocols. A guide to Methods and Application;* Academic Press: San Diego, 1990); ligase chain reaction (LCR) (Wu and Wallace. *Genomics* 1989, 4, 560; Landgren, et al. *Science* 1988, 241, 1077; and Barringer, et al. *Gene* 1990, 89, 117); transcription amplification (Kwoh et al. *Proc. Natl. Acad. Sci. USA* 1989, 86, 1173); and self-sustained sequence replication (Guatelli, et al. *Proc. Nat. Acad. Sci. USA* 1990, 87, 1874).

The nucleic acid labeling compound can be incorporated into a nucleic acid using a number of methods. For example, it can be directly attached to an original nucleic acid sample (e.g., mRNA, polyA mRNA, cDNA) or to an amplification product. Methods of attaching a labeling compound to a nucleic acid include, without limitation, nick translation, 3-end-labeling, ligation, in vitro transcription (IVT) or random priming. Where the nucleic acid is an RNA, a labeled riboligonucleotide is ligated, for example, using an RNA ligase such asT4 RNA Ligase. In *The Enzymes;* Uhlenbeck and Greensport, Eds.; Vol. XV, Part B, pp.31–58; and, Sambrook et al., pp. 5.66–5.69. Terminal transferase is used to add deoxy-, dideoxy- or ribonucleoside triphosphates (dNTPs, ddNTPs or NTPs), for example, where the nucleic acid is single stranded DNA.

The labeling compound can also be incorporated at an internal position of a nucleic acid. For example, PCR in the presence of a labeling compound provides an internally labeled amplification product. See, e.g., Yu et al. *Nucleic Acids Research* 1994, 22, 3226–3232. Similarly, IVT in the presence of a labeling compound can provide an internally labeled nucleic acid.

Probe Hybridization

The nucleic acid to which the labeling compound is attached can be detected after hybridization with a nucleic acid probe. Alternatively, the probe can be labeled, depending upon the experimental scheme preferred by the user. The probe is a nucleic acid, or a modified nucleic acid, that is either attached to a solid support or is in solution. It is complementary in structure to the labeled nucleic acid with which it hybridizes. The solid support is of any suitable material, including polystyrene based beads and glass chips. In a preferred embodiment, the probe or target nucleic acid is attached to a glass chip, such as a GeneChip® product (Affymetrix, Inc., Santa Clara, Calif.). See International Publication Nos. WO 97/10365, WO 97/29212, WO 97/27317, WO 95/11995, WO 90/15070, and U.S. Pat. Nos. 5,744,305 and 5,445,934 which are hereby incorporated by reference.

Because probe hybridization is often a step in the detection of a nucleic acid, the nucleic acid labeling compound must be of a structure that does not substantially interfere with that process. The steric and electronic nature of the labeling compound, therefore, is compatible with the binding of the attached nucleic acid to a complementary structure.

EXAMPLES

The following examples are offered to illustrate, but not to limit, the present invention.

General Experimental Details

Reagents were purchased from Aldrich Chemical Company (Milwaukee, Wis.) in the highest available purity. All listed solvents were anhydrous. Intermediates were characterized by $^1$H NMR and mass spectrometry.

EXAMPLE 1

Synthesis of Fluorescein- and Biotin-Labeled 1-(2, 3-Dideoxy-β-D-glycero-pentafuranosyl)imidazole-4-carboxamide Nucleotides 1-O-acetyl-5-O-(t-butyldimethylsilyl)-2,3-dideoxy-D-glycero-pentafuranose 1 (9.4 g, 34.2 mmole) (see, Duelholm, K.; Penderson, E. B., *Synthesis*, 1992, 1) and 1-trimethylsilyl-4-carboethoxyimidazole 2 (6.3 g; 34.2 mmole) (see, Pochet, S, et. al., *Bioorg. Med. Chem. Lett.,* 1995, 5, 1679) were combined in 100 ml dry DCM under Ar, and trimethylsilyl triflate catalyst (6.2 ml; 34.2 mmole) was added at 0° C. The solution was allowed to stir at room temperature for 5 hours and was then washed 3×with 100 ml of saturated aqueous NaHCO$_3$, 1×with saturated aqueous NaCl, dried with NaSO$_4$ and evaporated to provide 14 g of a crude mixture of four carboethoxyimidazole dideoxyriboside isomers (3a–d), corresponding to α and β-anomers of both N1 and N3 alkylation products. The isomeric products were purified and separated by flash chromatography (silica gel, EtOAc-hexane), in 52% total yield. The β-N1 isomer (2.2 g; 18% yield), was identified by $^1$H-NMR chemical shift and NOE data (see, Pochet, S, et. al., *Bioorg. Med. Chem. Lett.,* 1995, 5, 1679). Purified 3c (0.5 g; 1.4 mmole) was heated with a 20-fold excess of 1,4-diaminobutane (3.0 ml, 30 mmole) neat at 145° C. for 4 hours, and then the resulting mixture was diluted with 50 ml EtOAc, washed 3×with water, 1×with brine, and dried with NaSO$_4$ and evaporated to provide 500 mg (95%) of the imidazole-4-(4-aminobutyl)carboxamide dideoxyriboside 4 as a colorless oil. After coevaporation with toluene, 4 (393 mg; 0.75 mmole) was combined with trifluoroacetylimidazole (94 uL; 0.83 mmole) in 5 ml dry THF at 0° C., and stirred for 10 minutes. The solvent was evaporated, and the oily residue taken up in 50 ml EtOAc, extracted 2×with saturated aqueous NaHCO$_3$, 1×with saturated aqueous NaCl, dried with NaSO$_4$, and evaporated to yield 475 mg (99%) of the N-TFA protected nucleoside 5 as a colorless oil. The TBDMS group was removed by addition of excess triethylamine trihydrofluoride (2.3 ml; 14.4 mmole) in 20 ml dry THF and stirring overnight. The THF was evaporated in vacuo, the residue was taken up in 50 ml EtOAc and the solution was washed carefully with a 1:1 mixture of saturated aqueous NaHCO$_3$ and brine until neutral, then dried with NaSO$_4$, and evaporated to yield 340 mg (96%) of the 5 as a pale yellow oil. The NMR & MS data were consistent with the assigned structure.

Nucleoside 6 was converted to a 5'-triphosphate, deprotected, reacted with biotin-NH(CH$_2$)$_5$CO—NHS or 5-carboxyfluorescein-NHS and purified according to procedures reported elsewhere (see, Prober, J. M., et al., 1988, PCT 0 252 683 A2) to give the labeled nucleotides 8a,b in >95% purity by HPLC, $^{31}$P-NMR.

EXAMPLE 2

Synthesis of C3-Labeled 4-Aminopyrazolo[3,4-d] pyrimidine β-D-ribofuranoside Triphosphates The synthesis of 3-iodo-4-aminopyrazolo[3,4-d] pyrimidine ribofuranside (9) was carried out as described by H. B. Cottam, et al. 1993, J. Med. Chem. 36: 3424. Using the appropriate deoxyfuranoside precursors, both the 2'-deoxy and 2',3'-dideoxy nucleosides are prepared using analogous procedures. See, e.g., U. Neidballa & H. Vorbruggen 1974, J. Org. Chem. 39: 3654; K. L. Duehom & E. B. Pederson 1992, Synthesis 1992: 1). Alternatively, these are prepared by deoxygenation of ribofuranoside 9 according to established procedures. See, M. J. Robins et al. 1983 J. Am. Chem. Soc. 103: 4059; and, C. K. Chu, et al. 1989 J. Org. Chem. 54: 2217.

A protected propargylamine linker was added to the 4-aminopyrazolo[3,4-d]pyrimidine nucleoside (9) via organopalladium-mediated substitution to the 3-position of 4-aminopyrazolo[3,4-d]pyrimidine riboside using the procedure described by Hobbs (J. Org. Chem. 54: 3420; Science 238: 336.). Copper iodide (38 mg; 0.2 mmole), triethylamine (560 uL; 4.0 mmole), N-trifluoroacetyl-3-aminopropyne (700 uL; 6.0 mmole) and 3-iodo-4-aminopyrazolo[3,4-d] pyrimidine β-D-ribofuranoside (9) (H. B. Cottam, et al., 1993, J. Med. Chem. 36: 3424.) (786 mg; 2.0 mmole) were combined in 5 ml of dry DMF under argon. To the stirring mixture was added tetrakis(triphenylphosphine) palladium (0) (232 mg; 0.2 mmole). The solution became homogeneous within 10 minutes, and was left stirring for an additional 4 hours in the dark, at which time the reaction was diluted with 20 mL of MeOH-DCM (1:1), 3.3 g of Dowex AG-1 anion exchange resin (bicarbonate form) was added, and stirring was continued for another 15 minutes. The resin was removed by filtration and washed with MeOH-DCM (1:1), and the combined filtrates were evaporated to dryness. The residue was dissolved in 4 mL of hot MeOH, then 15 mL DCM was added and the mixture kept warm to maintain a homogeneous solution while it was loaded onto a 5 cm×25 cm column of silica gel that had been packed in 1:9 MeOH-DCM. The product (R$_f$~0.4, 6:3:1:1 DCM-EtOAc-MeOH-HOAc) was eluted with a 10–15–20% MeOH-DCM step gradient. The resulting pale yellow solid was washed 3×with 2.5ml of ice-cold acetonitrile, then 2×with ether and dried in vacuo to obtain 630 mg (75%) of 4-amino-3-(N-trifluoroacetyl-3-aminopropynyl)pyrazolo[3,4-d]pyrimidine β-D-ribofuranoside (10). Identity of the product was confirmed by $^1$H-nmr, mass spectrometry and elemental analysis.

The nucleoside was converted to a 5'-triphosphate (11), deprotected, reacted with oxysuccinimidyl-(N-biotinoyl-6-amino)hexanoate, or oxysuccinimidyl-(N-(fluorescein-5-carboxyl)-6-amino)hexanoate, and purified according to procedures reported elsewhere (Prober, J. M., et al., 1988, PCT 0 252 683 A2.) to give the biotin- and fluorescein-labeled nucleotides (12a, 12b) in >95% purity.

EXAMPLE 3

Synthesis of Fluorescein- and Biotin-N6-dideoxy-pyrazalo[3,4-d]pyrimidine Nucleotides 1-O-acetyl-5-O (t-butyldimethylsilyl)-2,3-dideoxy-D-glycero-pentofuranose (1) and 1-trimethylsilyl-4-chloropyrazolo[3,4-d]pyrimidine (13) were synthesized according to literature procedures. Duelholm, K. L.; Penderson, E. B., *Synthesis* 1992, 1–22; and, Robins, R. K., *J. Amer Chem Soc.* 1995, 78, 784–790. To 2.3 g (8.3 mmol) of 1 and 1.9 g (8.3 mmol, 1 eq) of 13 in 40 ml of dry DCM at 0° C. under argon was added slowly over 5 minutes 1.5 mL (8.3 mmol, 1 eq) of trimethylsilyl triflate. After 30 min. 4.2 ml (41.5 mmol, 5 eq) of 1,2-diaminobutane was added rapidly and the reaction was stirred at room temperature for 1 hr. The solvent was evaporated; the residue was dissolved in 50 ml of ethylacetate and washed with 50 ml of saturated aqueous. NaHCO$_3$ and dried over Na$_2$SO$_4$, filtered and the solvent evaporated to yield 4.2 g of a yellow foam. The foam was dissolved in 100 ml of diethyl ether and 100 ml of hexanes was added to precipitate the product as an oil. The solvent was decanted and the oil was dried under high vacuum to give 3.4 g of 15 as a pale yellow foam. HPLC, UV and MS data were consistent with a 2:1 mixture of the α- and β-anomers.

To the crude mixture of isomers (3.4 g, 8.1 mmol, ~50% pure) in 140 ml of dry THF at 0° C. under argon was added slowly 1.0 ml of 1-trifluoroacetylimidazole (8.9 mmol, 1.1 eq). The reaction was followed by RP-HPLC. An additional 5% of the acylating agent was added to completely convert the starting material to mixture of TFA-protected anomers. Bergerson, R. G.; McManis, J. S *J. Org. Chem* 1998, 53, 3108–3111. The reaction was warmed to room temperature, and then the solvent was evaporated to about 25 ml volume and diluted with 100 ml of ethylacetate. The solution was extracted twice with 25 ml of 1% aq. NaHCO$_3$, once with brine, then dried over Na$_2$SO$_4$ and evaporated to afford 3.4 g of yellow foam. The crude material was purified by flash chromatography on silica gel in EtOAc-hexanes to give 1.3 g of the α-anomer and 0.7 g of the β-anomer of 16 (50% total yield). The 1H-NMR and MS data were consistent with the assigned structure and stereochemistry.

To 1.3 g (2.5 mmol) of 16 (α-anomer) in 50 ml of dry THF under argon was added 1 ml (13.6 mmol) of triethylamine and 6.1 ml (37.5 mmol, 15 eq) of triethylamine trihydrofluoride. After stirring for 16 hr., the solvent was evaporated, and residual triethylamine trihydrofluoride removed under high vacuum. Pirrung, M. C.; et al. *Biorg. Med. Chem. Lett.* 1994, 4, 1345–1346. The residue was dissolved in 100 ml of ethylacetate and washed carefully with 4×100 ml of sat. aq. $NaHCO_3$, once with brine, then dried over $Na_2SO_4$ and evaporated to give 850 mg (95%) of white foam. 1H-NMR, UV and MS data were consistent with the assigned structure of the desilylated nucleoside, which was used in the next step without further purification.

The nucleoside was converted to the triphosphate using the Eckstein phosphorylation procedure (Ludwig, J. L. ; Eckstein, F. *J. Org. Chem.* 1989, 54, 631–635) followed by HPLC purification on a ResourceQ anion exchange column (buffer A is 20 mM Tri pH8, 20% $CH_3CN$ and buffer B is 20 mM Tris pH8, 1 M NaCl, 20% CH3CN). $^{31}P$-NMR, UV and MS data were consistent with the structure of the triphosphate. The trifluoroacetyl-protecting group was removed by treatment with excess $NH_4OH$ at 55° C. for 1 hr. followed by evaporation to dryness. The mass spectral data were consistent with the aminobutyl nucleotide 17. Without further purification, the nucleotide was treated with either Biotin-NHS esters or 5-Carboxyfluorescein-NHS as described elsewhere (Prober, J. M., et al., 1988, PCT 0 252 683 A2) to form the labeled nucleotides 18a–18d, respectively, which were purified by HPLC as described (Prober, J. M., et al., 1988, PCT 0 252 683 A2) except that, in the case of 18a, the buffer was 20 mM sodium phosphate pH6. The $^{31}P$-NMR and UV data were consistent with the structure of the labeled analogs.

EXAMPLE 4

Synthesis of N4-Labeled 1,2,4-Triazine-3-one β-D-ribofuranoside Triphosphates

To a solution of 1,2,4-triazole (6.7 g; 97 mmole) in 30 mL dry ACN was added $POCl_3$ (2.1 mL; 22 mmole) slowly with stirring under argon. After 30 minutes, the solution was cooled to 0° C., and a solution of triethylamine (21 mL; 150 mmole) and 2',3',5'-tri-O-acetyl-6-azauridine (19, 4.14 g; 11 mmole (commercially available from Aldrich Chemical Company)) in 10 mL ACN was added. After stirring for an additional hour at room temperature, the resulting solution of activated nucleoside was transferred dropwise to a stirring solution of 1,4-diaminobutane (46 g; 524 mmole) in 20 mL MeOH. The solvents were removed in vacuo, and the residue was taken up in water, neutralized with acetic acid, and evaporated again to dryness. The crude residue was purified by chromatography on silica gel (95:5 MeOH—$NH_4OH$), followed by preparative reverse-phase HPLC to yield 150 mg (0.45 mmole; 3%) of the aminobutyl nucleoside (21). This was converted directly to the TFA-protected nucleoside (22) by reaction with 1-trifluoroacetylimidazole (300 uL; 1.8 mmole) in 3 ml ACN at 0° C. for 2 hours, evaporating the solvent and purifying by flash chromatography (1:9 MeOH-DCM). Yield 175 mg (0.42 mmole; 93%). Identity of the product was confirmed by $^1H$-nmr and mass spectrometry.

The nucleoside was converted to a 5'-triphosphate, deprotected, reacted with oxysuccinimidyl-(N-biotinoyl-6-amino)hexanoate, or oxysuccinimidyl-(N-(fluorescein-5-carboxyl)-6-amino)hexanoate, and purified according to procedures reported elsewhere (Prober, J. M., et al., 1988, PCT 0 252 683 A2.) to give the biotin- and fluorescein-labeled nucleotides (23a, 23b) in >95% purity.

EXAMPLE 5

Synthesis of Biotin and Fluorescein C5-Labeled 1,2,4-Triazine-3,5-dione Riboside Triphosphates 5-Formyl-6-azauracil (24) is prepared according to literature procedures. See, Scopes, D. I. C. 1986, J. Chem. Med., 29, 809–816, and references cited therein. Compound 24 is reacted with the phosphonium ylide of 25, which is formed by treating 25 with catalytic t-butoxide, to provide the phthalimidoyl-protected allylamine 26. Protected allylamine 26 is ribosylated to provide β-anomer 28 upon reaction of 26 with β-D-pentofuranoside 27 (commercially available from Aldrich) according to the procedure of Scopes et al. 1986, J. Chem. Med., 29, 809–816. β-ribonucleoside 28 is deprotected with anhydrous hydrazine in THF to provide allylamine 29. Reaction of primary amine 29 with trifluoroacetylimidazole in THF affords the protected amine 30.

Nucleoside 30 is converted to a 5'-triphosphate, deprotected, reacted with oxysuccinimidyl-(N-biotinoyl-6-amino)hexanoate or oxysuccinimidyl-(N-(fluorescein-5-carboxy)-6-amino)hexanoate and purified according to procedures reported elsewhere (Prober, J. M., et al. 1988, PCT 0 252 683 A2), giving, respectively, the biotin- and fluorescein-labeled nucleotides 31a and 31b.

EXAMPLE 6

Synthesis of Biotin and Fluorescein C5-Labeled 5-Amino-1,2,4-triazine-3-one Riboside Triphosphates β-ribonucleoside 28, described above, is treated with $SOCl_2$ or $POCl_3$ and subsequently reacted with ammonia to provide the 4-amino-1,3,6-triazine nucleoside 32. The phthalimide group of 32 is removed upon reaction with hydrazine, and the resulting primary amine is protected to afford nucleoside 33. Nucleoside 33 is converted to a 5'-triphosphate, deprotected, reacted with oxysuccinimidyl-(N-biotinoyl-6-amino)hexanoate or oxysuccinimidyl-(N-(fluorescein-5-carboxy)-6-amino)hexanoate and purified according to procedures reported elsewhere (Prober, J. M., et al. 1988, PCT 0 252 683 A2), giving, respectively, the biotin- and fluorescein-labeled nucleotides 34a and 34b.

EXAMPLE 7

Procedure for HPLC Analysis of Enzymatic Incorporation of Modified Nucleotides

Reaction Conditions
TdT
3 uM $dT_{16\ template}$
15(30) uM NTP
40 U TdT (Promega)
1×buffer, pH 7.5 (Promega)

Procedure: incubate 1 hr. at 37° C., then for 10 min. at 70° C., followed by the addition of EDTA (2 mM final concentration) in a volume of 50 uL HPLC Analysis
Materials and Reagents
4.6 mm×250 mm Nucleopac PA-100 ion-exchange column (Dionex)
buffer A: 20 mM NaOH (or 20 mM Tris pH 8, in the case of TdT incorporation of nucleotide triphoshates that are not dye-labeled)

buffer B: 20 mM NaOH, 1M NaCl (or 20 mM Tris pH 8, 1M NaCl, in the case of TdT incorporation of nucleotide triphoshates that are not dye-labeled)

General Procedure

Dilute the reaction with 50 uL of buffer A. Inject 50 uL of this sample onto the HPLC column and fractionate using a gradient of 5 to 100% buffer B over 30 minutes at a flow rate of 1 mL/min. Detect the peaks simultaneously at 260 nm absorbance and the absorbance maximum of the dye (or the fluorescence emission maximum of the dye).

The incorporation efficiency is expressed as the fraction of oligonucleotide that is labeled. This number is determined by dividing the peak area measured at 260 nm absorbance of the labeled oligonucleotide by the sum of the peak areas of the unlabeled and labeled oligonucleotide. (The retention time of fluorescein-labeled $dT_{16}$ is on the order of 2 to 3 min. longer than the unlabeled $dT_{16}$.) The error in this type of assay is about 10%. The percentage labeling efficiency for 4 types of nucleic acid labeling compounds is shown below in Table 1 and Table 2.

TABLE 1

| R = | B = | Compound | % Labeling Efficiency [TdT] = 40 U | % Labeling Efficiency [TdT] = 160 U |
|---|---|---|---|---|
| H | HN—[CH₂]₄NHX (pyrazolopyrimidine) | X = -BIOTIN (18a) | 48 | 100 |
| | | —CO(CH₂)₅NH-BIOTIN (18b) | 41 | 96 |
| | | —CO(CH₂)₅NHCO(CH₂)₅NH-BIOTIN (18c) | 57 | 94 |
| | | 5-carboxyFluorescein (18d) | 60 | 98 |
| OH | NHC(COH₂)₅NHX (alkynyl-aminopyrazolopyrimidine) | X = -BIOTIN (12a) | 25 | 84 |
| | | 5-carboxyFluorescein (12b) | 53 | 97 |
| H | HN(CH₂)₄NHX (pyrazole carboxamide) | X = —CO(CH₂)₅NH-BIOTIN (8a) | 88 | 94 |
| | | 5-carboxyFluorescein (8b) | 94 | 97 |
| OH | HN(CH₂)₄NHC(O₂H)₅NHX (triazinone) | X = -BIOTIN (23a) | 47 | 85 |
| | | 5-carboxyFluorescein (23b) | 67 | 98 |

TABLE 2

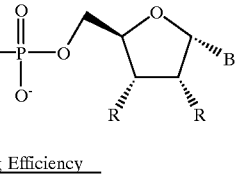

% Labeling Efficiency

| | | | [TdT] = | | |
|---|---|---|---|---|---|
| R | B | X | 40 U | 80 U | 160 U |
| H | 1-methyl-imidazole-4-C(O)NH(CH₂)₄NH—X | C(O)(CH₂)₅NH-Biotin | — | 76 | 89 |
| H | 1-methyl-imidazole-4-C(O)NH(CH₂)₄NH—X | 5-carboxy-fluorescein | — | 22 | 39 |
| H | 4-[NH(CH₂)₄NH—X]-1-methyl-pyrazolo[3,4-d]pyrimidine | 5-carboxy-fluorescein | 8 | — | — |
| H | 4-[NH(CH₂)₄NH—X]-1-methyl-pyrazolo[3,4-d]pyrimidine | trifluoroacetyl | 55 | — | — |
| H | 4-[NH(CH₂)₄NH—X]-1-methyl-pyrazolo[3,4-d]pyrimidine | C(O)(CH₂)₅NH-trifluoroacetyl | 49 | — | — |

EXAMPLE 8

Hybridization Studies of Labeled Imidazole Carboxamide ("ITP") and 4-Aminopyrazolo[3,4-d]pyrimidine ("APPTP") Nucleotides The performance of the labeled imidazolecarboxamide and 4-aminopyrazolo[3,4-d]pyrimidine nucleotides was evaluated in a p53 assay using standard GeneChip® product protocols (Affymetrix, Inc., Santa Clara, Calif.), which are described, for example, in detail in the GeneChip® p53 assay package insert. The sample DNA used in these experiments was the plasmid "p53mut248." The labeled nucleotide analog was substituted for the usual labeling reagent (Fluorescein-N6-ddATP or Biotin-M-N6-ddATP (wherein M=aminocaproyl), from NEN, part #'s NEL-503 and NEL-508, respectively). Labeling reactions were carried out using both the standard amount of TdT enzyme specified in the assay protocol (25 U) and with 100 U of enzyme. After labeling, Fluorescein-labeled targets were hybridized to the arrays and scanned directly. In experiments using the biotin-labeled targets, the GeneChip® chips were stained in a post-hybridization step with a phycoerythrin-streptavidin conjugate (PE-SA), prior to scanning, according to described procedures (Science 280: 1077–1082 (1998)).

Figure 9:
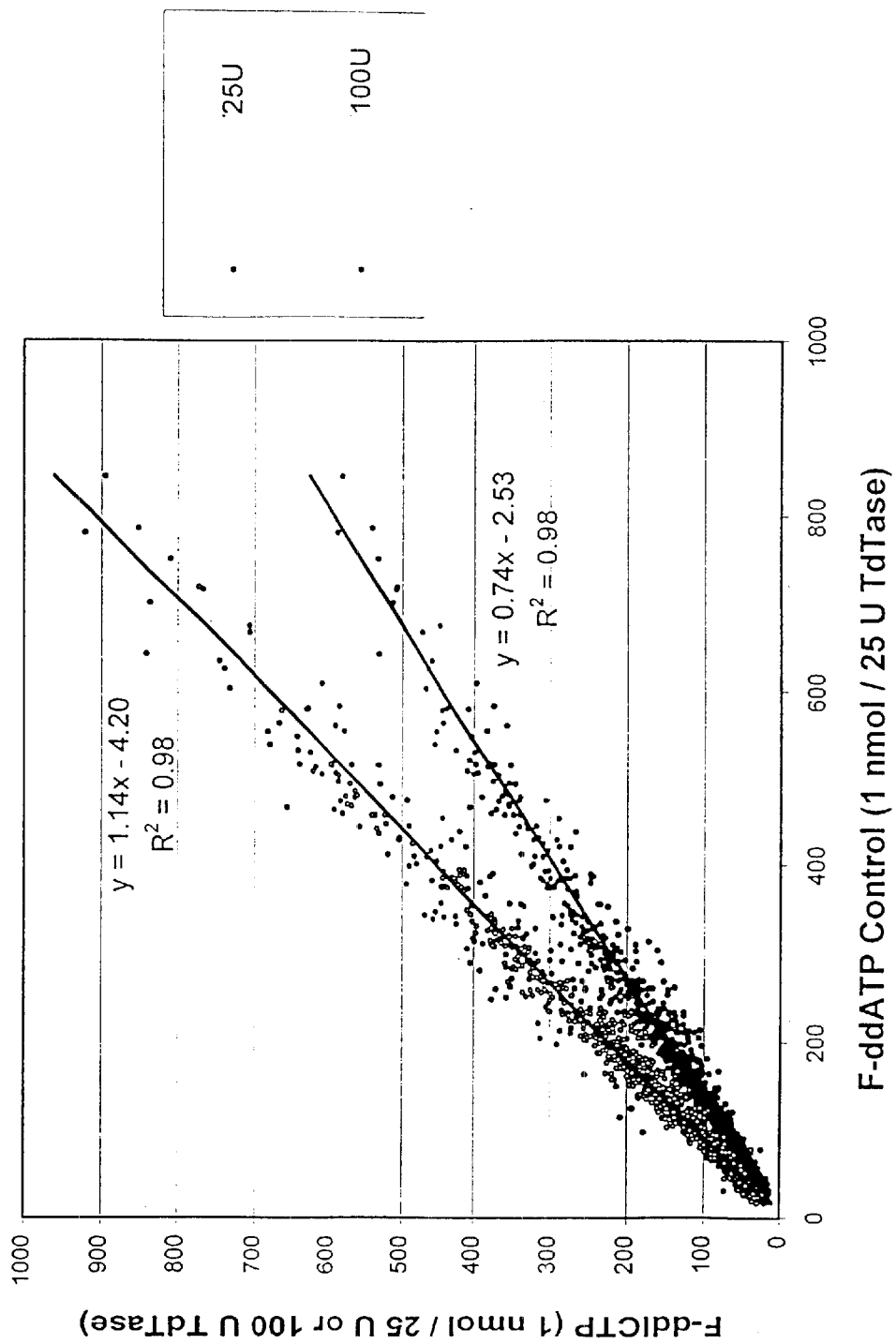
FIG. 9 shows graphical comparisons of observed hybridization fluorescence intensities using Fluorescein-ddITP and Fluorescein-ddATP.

FIG. 9 shows comparisons of the observed hybridization fluorescence intensities for the 1300 bases called in the "Unit-2" part of the chip. In the lower plot, intensities for the Fluorescein-ddITP (8b) labeled targets are plotted against those for the standard Fluorescein-N6-ddATP labeled targets (control), both at 25 U of TdT. The observed slope of ~0.75 indicates that the labeling efficiency of 8b was about 75% of that of Fluorescein-N6-ddATP under these conditions. In the upper plot, the same comparison is made, except that 100 U of TdT was used in the 8b labeling reaction. The slope of ~1.1 indicates equivalent or slightly better labeling than the standard Fluorescein-N6-ddATP/25 U control reaction.

Figure 10:
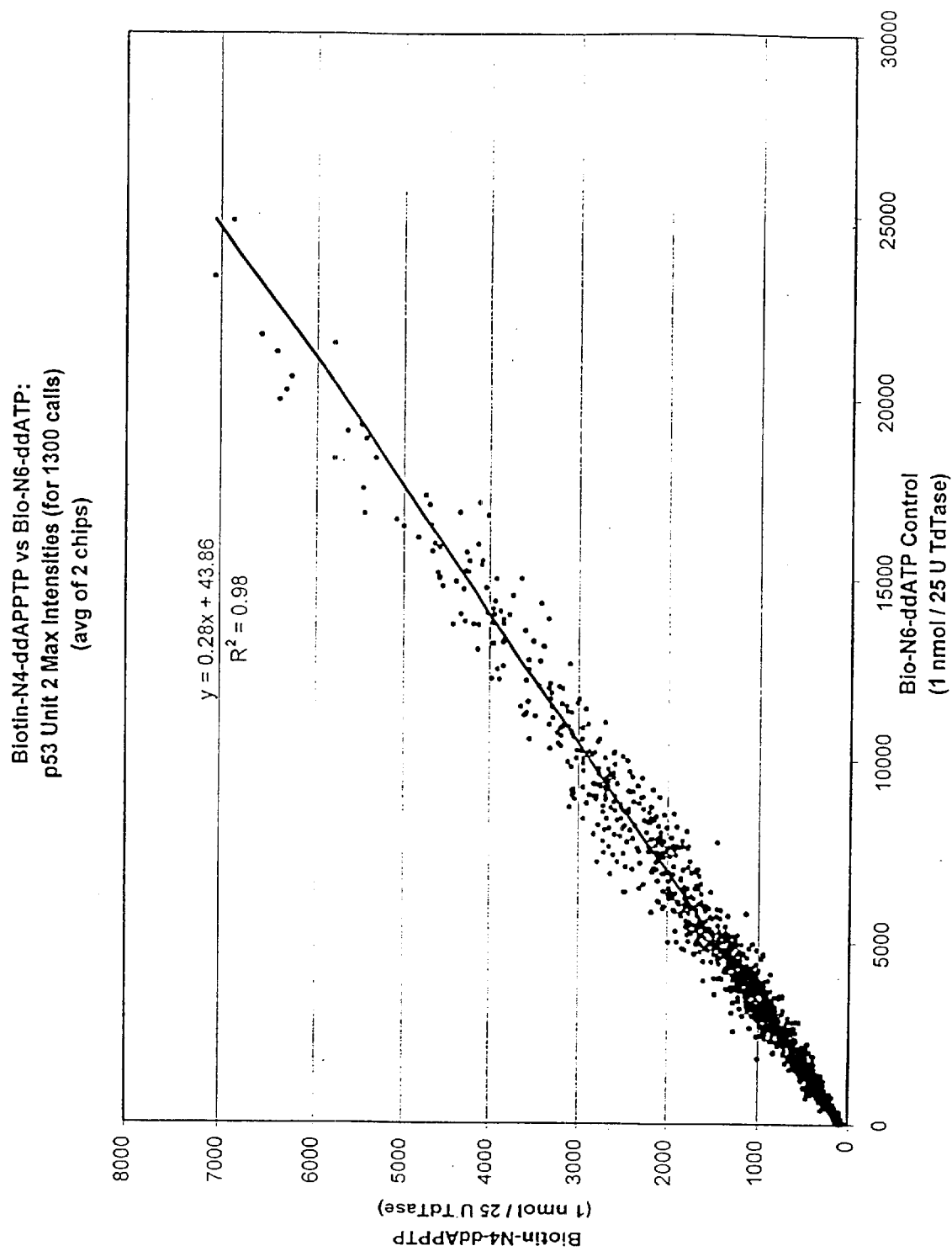
FIG. 10 shows a graphical comparison of observed hybridization fluorescence intensities using Biotin-(M)$_2$-ddAPTP (wherein M=aminocaproyl) and Biotin-N6-ddATP.

FIG. 10 shows comparisons of the observed hybridization fluorescence intensities for the 1300 bases called in the "Unit-2" part of the chip. Intensities for the Biotin-(M)$_2$-ddAPPTP (18c, M=aminocaproyl linker; referred to as Biotin-N4-ddAPPTP in FIG. 10) labeled targets (after PE-SA staining) are plotted against those for the standard Biotin-M-N6-ddATP labeled targets (control), both at 25 U of TdT. The observed slope of ~0.3 indicates that the labeling efficiency with Biotin-(M)$_2$-ddAPPTP (18c) was about 30% of that of Biotin-M-N6-ddATP under these conditions.

Figure 11:
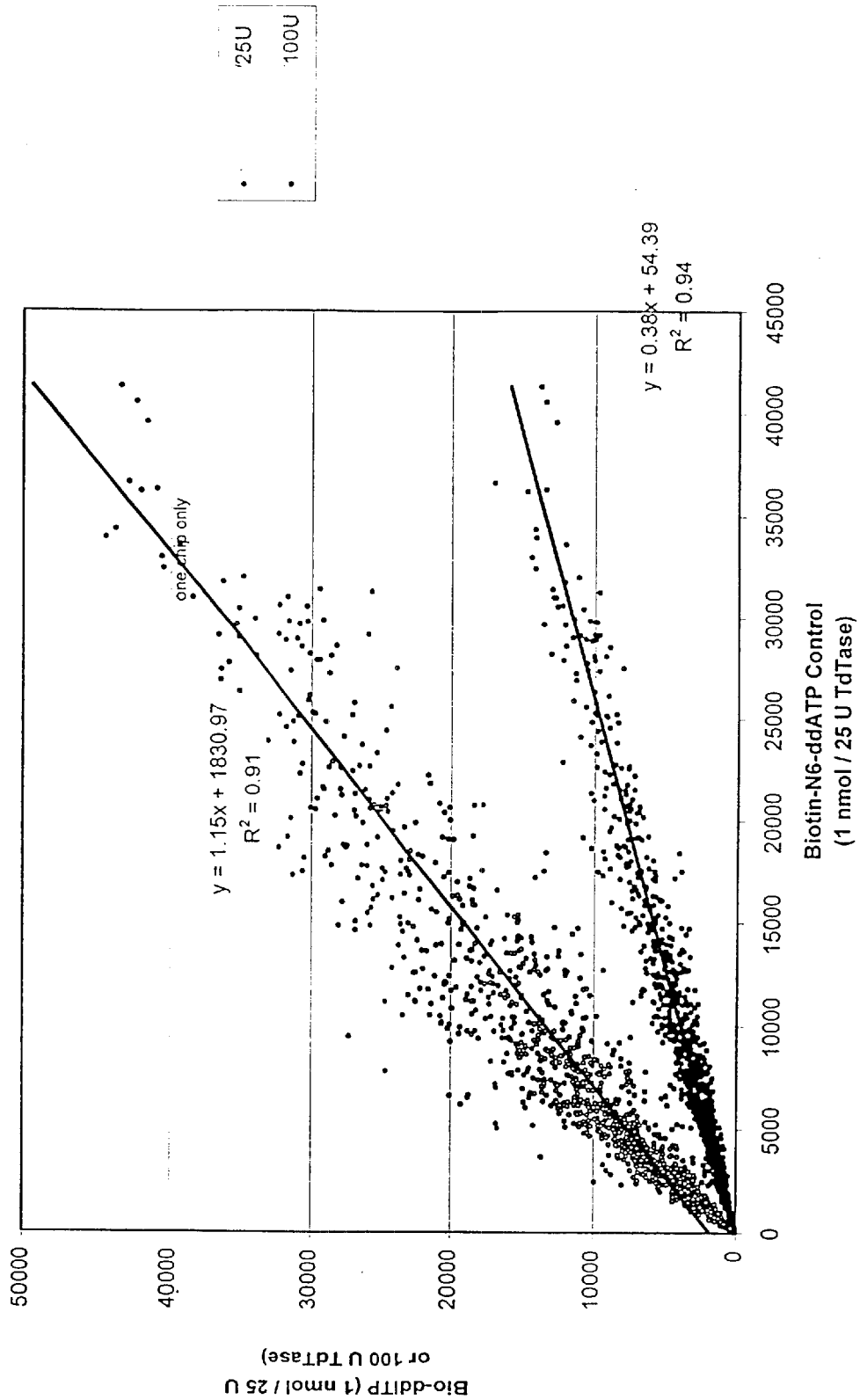
FIG. 11 shows graphical comparisons of observed hybridization fluorescence intensities using Biotin-M-ddITP (wherein M=aminocaproyl) and Biotin-N6-ddATP.

FIG. 11 shows comparisons of the observed hybridization fluorescence intensities for the 1300 bases called in the "Unit-2" part of the chip. In the lower plot, intensities for the Biotin-M-ddITP (8a, M=aminocaproyl; referred to as Bio-ddITP in FIG. 11) labeled targets are plotted against those for the standard Biotin-M-N6-ddATP labeled control targets, both at 25 U of TdT. The observed slope of ~0.4 indicates that the labeling efficiency with 8a was about 40% of that of Biotin-M-N6-ddATP under these conditions. In the upper plot, the same comparison is made, except that 100 U of TdT was used in the 8a labeling reaction. The slope of ~1.1 indicates equivalent or slightly better labeling than the standard Biotin-M-N6-ddATP/25 U control reaction.

Figure 12:
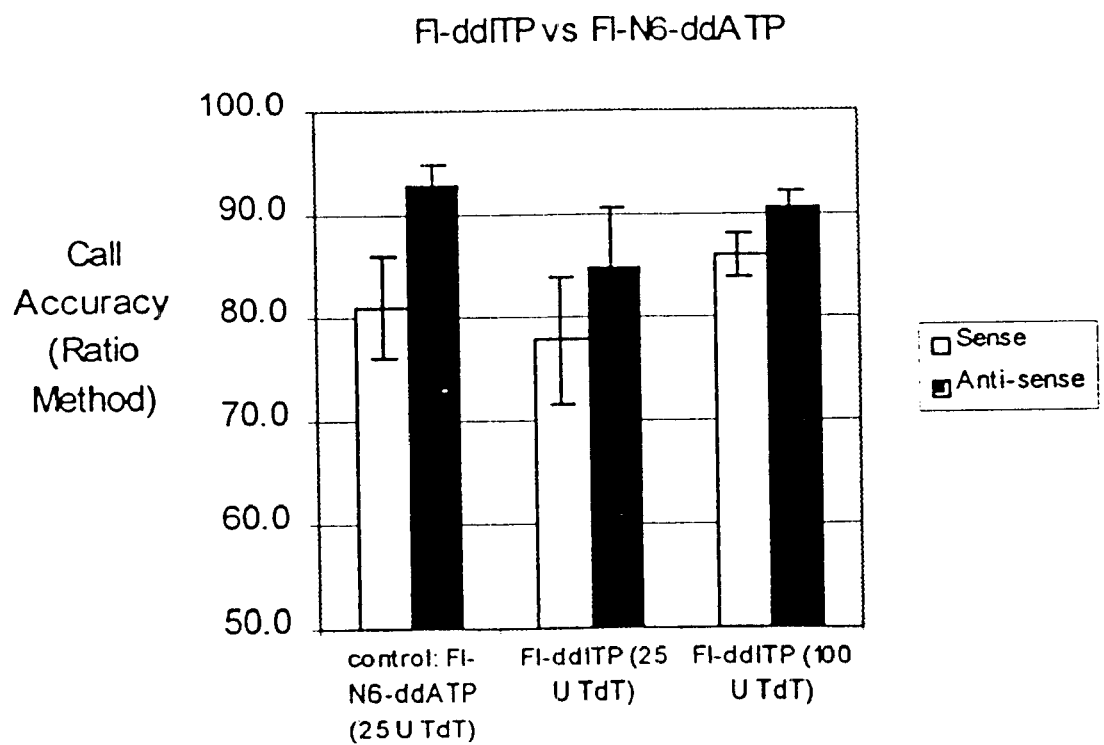
FIG. 12 shows a graphical comparison of overall re-sequencing (base-calling) accuracy using Fluorescein-ddITP and Fluorescein-N6-ddATP labeled targets.
Figure 13:
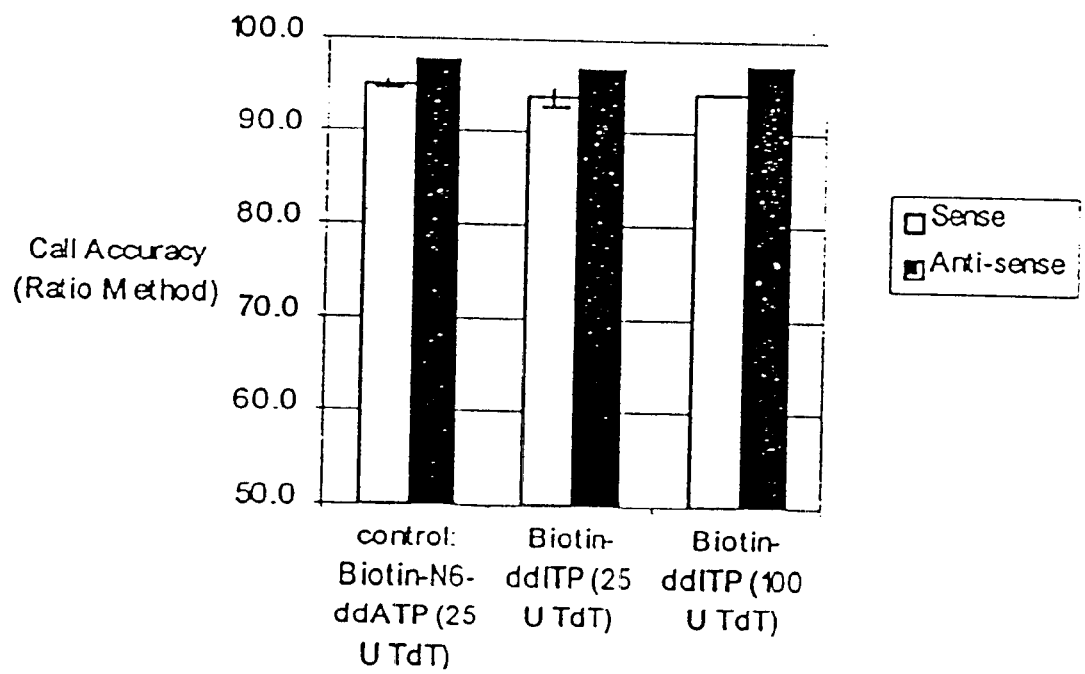
FIG. 13 shows a graphical comparison of overall re-sequencing accuracy using Biotin-M-ddITP (wherein M=aminocaproyl) and Biotin-N6-ddATP.
Figure 14:
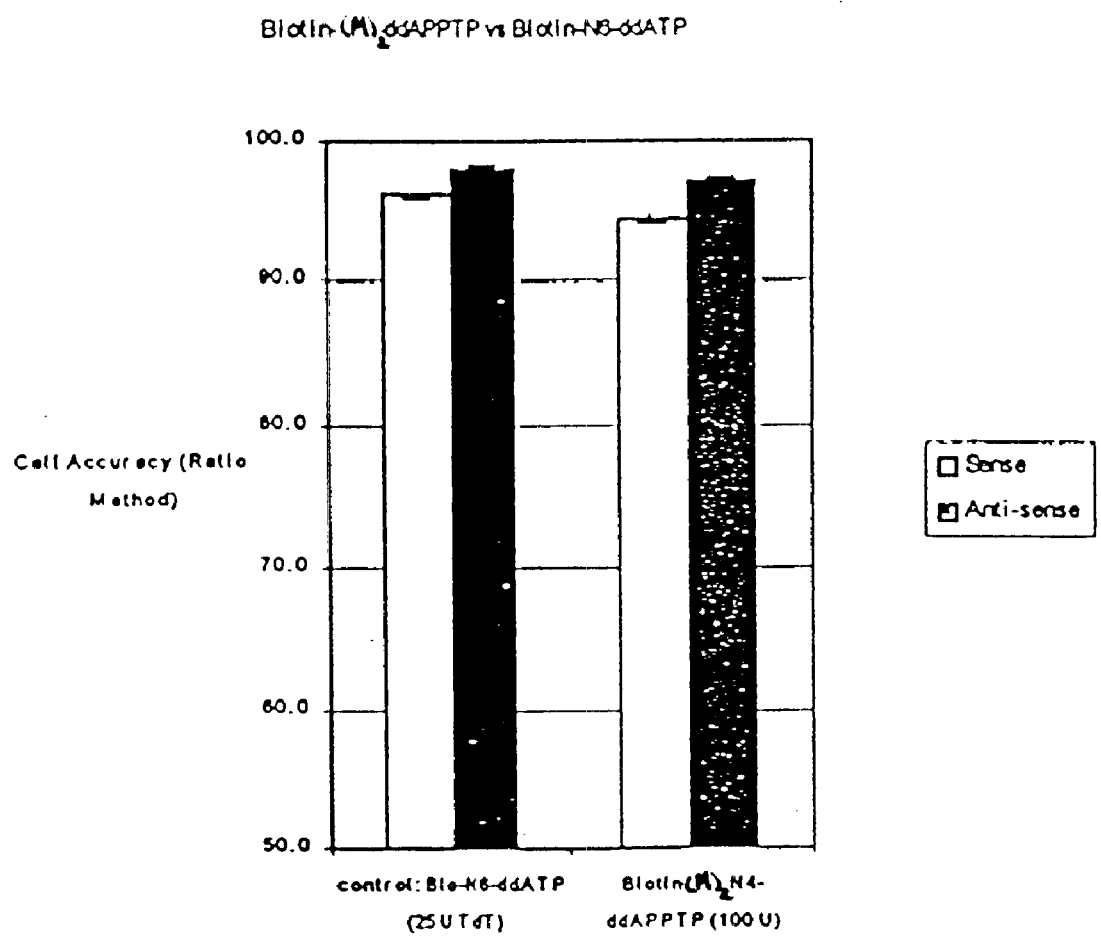
FIG. 14 shows a graphical comparison of re-sequencing accuracy using Biotin-(M)$_2$-ddAPPTP (wherein M=aminocaproyl) and Biotin-N6-ddATP.

FIG. 12 shows a comparison of the overall re-sequencing (base-calling) accuracy, for both strands, obtained using Fluorescein-ddITP labeled targets at both 25 U and 100 U of TdT, as well as the standard Fluorescein-N6-ddATP/25 U TdT labeled "control" targets. FIG. 13 shows a similar comparison for the targets labeled with biotin-M-ddITP (8a; referred to as Biotin-ddITP in FIG. 13) and biotin-M-N6-ddATP "control," followed by PE-SA staining. FIG. 14 shows a comparison of re-sequencing accuracy using Biotin-(M)$_2$-ddAPPTP/100 U TdT and Biotin-M-N6-ddATP/25 U TdT. These data indicate that labeled imidazolecarboxamide and 4-aminopyrazolo[3,4-d]pyrimidine dideoxynucleotide analogs can be used for DNA target labeling in hybridization-based assays and give equivalent performance to the standard labeled-N6-ddATP reagent.

EXAMPLE 9

The performance of the biotin-labeled imidazolecarboxamide and 4-aminopyrazolo[3,4-d]pyrimidine nucleotides ("biotin-M-ITP" (8a) and "biotin-(M)$_2$-APPTP" (18c)) was evaluated using a single-nucleotide polymorphism genotyping GeneChip® chip array. Published protocols (D. G. Wang, et al., 1998, Science 280: 1077–82.) were used in these experiments, except for the following variations: 1) labeling reactions were carried out using both the standard amount of TdT enzyme specified in the published protocol (15 U), or three-fold (45 U) enzyme; 2) substitution of the labeled nucleotide analog for the standard labeling reagent (Biotin-N6-ddATP, from NEN: P/N NEL-508); 3) the labeled nucleotide analog was used at either twice the standard concentration specified in the published protocol (25 uM), or at six-fold (75 uM). After labeling, biotin-labeled targets were hybridized to the arrays, stained with a phycoerythrin-streptavidin conjugate (PE-SA), and the array was scanned and analyzed according to the published procedure.

The data is shown in the Table 2 below. As indicated by the mean intensities of the observed hybridization signal (averaged over the entire array), labeling efficiency with biotin-M-ITP (8a) at 25 uM was as good as Biotin-N6-ddATP at 12.5 uM, and even higher intensity was gained by using 8a at 75 uM (entries 1–3; 7,8). Compared with the control, this analog provided equivalent or better assay performance, expressed as the ratio of correct base calls. Somewhat lower mean signal intensities are observed with biotin-(M)$_2$-APPTP (18c), reflecting the lower incorporation efficiency of this analog, but equivalent assay performance could still be achieved with this analog, using somewhat higher enzyme and nucleotide concentrations (entries 3–6).

TABLE 3

Comparison of Polymorphism Chip Data

| Entry | Sample | Nucleotide | [Nucleotide] | Units TdT | Mean Intensity | Correct Base Call Ratio |
|---|---|---|---|---|---|---|
| 1 | A | Biotin-M-ddIcTP (8a) | 75 | 15 | 164 | 0.98 |
| 2 | A | Biotin-M-ddIcTP (8a) | 75 | 45 | 235 | 0.98 |
| 3 control | B | Biotin-N6-M-ddATP (NEL 508) | 12.5 | 15 | 138 | 0.95 |
| 4 | B | Biotin-N4-(M)$_2$-ddAppTP (18c) | 25 | 15 | 37 | 0.88 |
| 5 | B | Biotin-N4-(M)$_2$-ddAppTP (18c) | 75 | 15 | 35 | 0.92 |
| 6 | B | Biotin-N4-(M)$_2$-ddAppTP (18c) | 75 | 45 | 87 | 0.95 |
| 7 | B | Biotin-M-ddIcTP (8a) | 25 | 15 | 116 | 0.95 |
| 8 | B | Biotin-M-ddIcTP (8a) | 75 | 15 | 149 | 0.95 |

All patents, patent applications, and literature cited in the specification are hereby incorporated by reference in their entirety. In the case of any inconsistencies, the present disclosure, including any definitions therein will prevail.

The invention has been described with reference to various specific and preferred embodiments and techniques. However, it should be understood that many variations and modifications may be made while remaining within the spirit and scope of the invention.

What is claimed is:

1. A nucleic acid labeling compound comprising the formula:

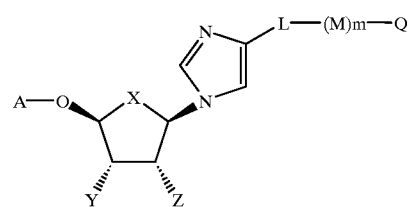

wherein A is H or a functional group that permits the attachment of the nucleic acid labeling compound to a nucleic acid;

X is O, or S,

Y is H, $N_3$, F, $OR_9$, $SR_9$ or $NHR_9$, wherein $R_9$ is H, alkyl or aryl;

Z is H, $N_3$, F or $OR_{10}$, wherein $R_{10}$ is H, alkyl or aryl;

L is amido alkyl; Q is a detectable moiety; and

M is a connecting group, wherein m is an integer ranging from 0 to about 3.

2. A nucleic acid labeling compound according to claim 1, wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —C(O)NH$(CH_2)_n$NH—, wherein n is an integer ranging from about 2 to about 10; Q is biotin or a carboxyfluorescein; and M is —CO$(CH_2)_5$NH—, wherein m is 1 or 0.

3. A nucleic acid labeling compound according to claim 2, wherein Y is H or OH; Z is H or OH; L is —C(O)NH$(CH_2)_4$NH—; Q is biotin; and M is —CO$(CH_2)_5$NH, wherein m is 1.

4. A nucleic acid labeling compound according to claim 2, wherein Y is H or OH; Z is H or OH; L is —C(O)NH$(CH_2)_4$NH—; Q is 5-carboxyfluorescein; and m is 0.

5. A nucleic acid labeling compound according to claim 2, wherein A is H; Y is H; Z is H; L is —C(O)NH$(CH_2)_4$NH—; Q is biotin; and M is —CO$(CH_2)_5$NH, wherein m is 1.

6. A nucleic acid labeling compound according to claim 2, wherein A is $H_4O_9P_3$—; Y is H; Z is H; L is —C(O)NH$(CH_2)_4$NH—; Q is biotin; and M is —CO$(CH_2)_5$NH, wherein m is 1.

7. A nucleic acid labeling compound according to claim 2, wherein A is H; Y is H; Z is H; L is —C(O)NH$(CH_2)_4$NH—; Q is 5-carboxyfluorescein; and m is 0.

8. A nucleic acid labeling compound according to claim 2, wherein A is $H_4O_9P_3$—; Y is H; Z is H; L is —C(O)NH$(CH_2)_4$NH—; Q is 5-carboxyfluorescein; and m is 0.

9. A method of synthesizing a labeled nucleic acid comprising attaching a nucleic add labeling compound according to claim 2 to a nucleic acid.

10. A nucleic acid labeling compound comprising the formula:

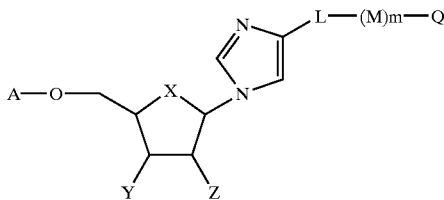

wherein A is H or a functional group that permits the attachment of the nucleic acid labeling compound to a nucleic acid;

X is O, or S,

Y is H, $N_3$, F, $OR_9$, $SR_9$ or $NHR_9$, wherein $R_9$ is H, alkyl or aryl;

Z is H, $N_3$, F or $OR_{10}$, wherein $R_{10}$ is H, alkyl or aryl;

L is amido alkyl; Q is a detectable moiety; and

M is a connecting group, wherein m is an integer ranging from 0 to about 3.

11. A nucleic acid labeling compound according to claim 10, wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —C(O)NH$(CH_2)_n$NH—, wherein n is an integer ranging from about 2 to about 10; Q is biotin or a carboxyfluorescein; and M is —CO$(CH_2)_5$NH—, wherein m is 1 or 0.

12. A nucleic acid labeling compound according to claim 11, wherein Y is H or OH; Z is H or OH; L is —C(O)NH$(CH_2)_4$NH—; Q is biotin; and M is —CO$(CH_2)_5$NH, wherein m is 1.

13. A nucleic acid labeling compound according to claim 11, wherein Y is H or OH; Z is H or OH; L is —C(O)NH$(CH_2)_4$NH—; Q is 5-carboxyfluorescein; and m is 0.

14. A nucleic acid labeling compound according to claim 11, wherein A is H; Y is H; Z is H; L is —C(O)NH$(CH_2)_4$NH—; Q is biotin; and M is —CO$(CH_2)_5$NH, wherein m is 1.

15. A nucleic acid labeling compound according to claim 11, wherein A is $H_4O_9P_3$—; Y is H; Z is H; L is —C(O)NH$(CH_2)_4$NH—; Q is biotin; and M is —CO$(CH_2)_5$NH, wherein m is 1.

16. A nucleic acid labeling compound according to claim 11, wherein A is H; Y is H; Z is H; L is —C(O)NH$(CH_2)_4$NH—; Q is 5-carboxyfluorescein; and m is 0.

17. A nucleic acid labeling compound according to claim 11, wherein A is $H_4O_9P_3$—; Y is H; Z is H; L is —C(O)NH$(CH_2)_4$NH—; Q is 5-carboxyfluorescein; and m is 0.

18. A method of synthesizing a labeled nucleic acid comprising attaching a nucleic acid labeling compound according to claim 11 to a nucleic acid.

19. A nucleic acid labeling compound comprising the formula:

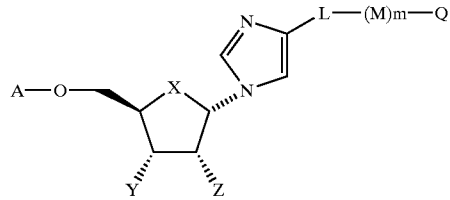

wherein A is H or a functional group that permits the attachment of the nucleic acid labeling compound to a nucleic acid;

X is O, or S,

Y is H, $N_3$, F, $OR_9$, $SR_9$ or $NHR_9$, wherein $R_9$ is H, alkyl or aryl;

Z is H, $N_3$, F or $OR_{10}$, wherein $R_{10}$ is H, alkyl or aryl;

L is amido alkyl; Q is a detectable moiety; and

M is a connecting group, wherein m is an integer ranging from 0 to about 3.

20. A nucleic acid labeling compound according to claim 19, wherein A is H or $H_4O_9P_3$—; X is O; Y is H or $OR_9$, wherein $R_9$ is H, alkyl or aryl; Z is H, $N_3$, F or $OR_{10}$, wherein $R_{10}$ is H, alkyl or aryl; L is —C(O)NH$(CH_2)_n$NH—, wherein n is an integer ranging from about 2 to about 10; Q is biotin or a carboxyfluorescein; and M is —CO$(CH_2)_5$NH—, wherein m is 1 or 0.

21. A nucleic acid labeling compound according to claim 20, wherein Y is H or OH; Z is H or OH; L is —C(O)NH$(CH_2)_4$NH—; Q is biotin; and M is —CO$(CH_2)_5$NH, wherein m is 1.

22. A nucleic acid labeling compound according to claim 20, wherein Y is H or OH; Z is H or OH; L is —C(O)NH(CH$_2$)$_4$NH—; Q is 5-carboxyfluorescein; and m is 0.

23. A nucleic acid labeling compound according to claim 20, wherein A is H; Y is H; Z is H; L is —C(O)NH(CH$_2$)$_4$NH—; Q is biotin; and M is —CO(CH$_2$)$_5$NH, wherein m is 1.

24. A nucleic acid labeling compound according to claim 20, wherein A is H$_4$O$_9$P$_3$—; Y is H; Z is H; L is —C(O)NH(CH$_2$)$_4$NH—; Q is biotin; and M is —CO(CH$_2$)$_5$NH—, wherein m is 1.

25. A nucleic acid labeling compound according to claim 20, wherein A is H; Y is H; Z is H; L is —C(O)NH(CH$_2$)$_4$NH—; Q is 5-carboxyfluorescein; and m is 0.

26. A nucleic acid labeling compound according to claim 20, wherein A is H$_4$O$_9$P$_3$—; Y is H; Z is H; L is —C(O)NH(CH$_2$)$_4$NH—; Q is 5-carboxyfluorescein; and m is 0.

27. A method of synthesizing a labeled nucleic acid comprising attaching a nucleic acid labeling compound according to claim 20 to a nucleic acid.

* * * * *